United States Patent
Long et al.

(10) Patent No.: US 8,761,940 B2
(45) Date of Patent: Jun. 24, 2014

(54) TIME BLOCK MANIPULATION FOR INSULIN INFUSION DELIVERY

(75) Inventors: James R. Long, Fishers, IN (US); D. Bradley Markisohn, Indianapolis, IN (US); William Levy, Brownsburg, IN (US); Leon R. Organ, III, Indianapolis, IN (US); Jason M. Bush, Fishers, IN (US); Kristin M. Westerfield, Fortville, IN (US); Hans P. Jensen, Fishers, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 712 days.

(21) Appl. No.: 12/905,431

(22) Filed: Oct. 15, 2010

(65) Prior Publication Data
US 2012/0095310 A1    Apr. 19, 2012

(51) Int. Cl.
*A61B 5/145*   (2006.01)
*G09B 19/00*   (2006.01)

(52) U.S. Cl.
USPC .............. 700/266; 700/17; 700/18; 700/83; 702/19; 702/22; 702/31; 702/32; 600/365

(58) Field of Classification Search
USPC ........ 700/266, 17, 18, 83; 702/19, 22, 31, 32; 600/365
See application file for complete search history.

(56) References Cited

U.S. PATENT DOCUMENTS

| | | | |
|---|---|---|---|
| 7,837,647 B2 | 11/2010 | Estes et al. | |
| 2005/0055243 A1 | 3/2005 | Arndt et al. | |
| 2006/0047192 A1 | 3/2006 | Hellwig et al. | |
| 2007/0033074 A1* | 2/2007 | Nitzan et al. | 705/3 |
| 2008/0040449 A1* | 2/2008 | Grant et al. | 709/218 |
| 2008/0108888 A1* | 5/2008 | Brown | 600/365 |
| 2008/0114229 A1* | 5/2008 | Brown | 600/365 |
| 2009/0030733 A1 | 1/2009 | Cohen et al. | |
| 2009/0036828 A1 | 2/2009 | Hansen et al. | |
| 2009/0147011 A1 | 6/2009 | Buck et al. | |
| 2009/0150177 A1 | 6/2009 | Buck et al. | |
| 2009/0164239 A1 | 6/2009 | Hayter et al. | |
| 2010/0064236 A1 | 3/2010 | Buck et al. | |
| 2010/0064243 A1 | 3/2010 | Buck et al. | |
| 2010/0064257 A1 | 3/2010 | Buck et al. | |
| 2010/0077198 A1 | 3/2010 | Buck et al. | |
| 2010/0122074 A1 | 5/2010 | Drucker et al. | |
| 2010/0167385 A1 | 7/2010 | Celentano et al. | |
| 2010/0274592 A1 | 10/2010 | Nitzan et al. | |

* cited by examiner

*Primary Examiner* — Shogo Sasaki
(74) *Attorney, Agent, or Firm* — Harness, Dickey

(57) ABSTRACT

The present teachings provide a system for modifying insulin therapy support parameters such as warning limit data and time block data on a hand-held diabetes management device. The system can include a graphical user interface module that creates a graphical user interface having a plurality of bar structures positionable on or between a first line that indicates an upper limit and a second line that illustrates a lower limit. Each of the bar structures can have a first side that indicates a start time of a time window opposite a second side that indicates an end time of the time window and a third side that indicates a lower target value for a blood glucose level opposite a fourth side that indicates an upper target value for the blood glucose level. The bar structures, the first line and the second line can be adjustable by a user input.

19 Claims, 24 Drawing Sheets

TIME BLOCK MANIPULATION FOR INSULIN INFUSION DELIVERY

FIELD

The present disclosure relates generally to diabetes management devices having adjustable insulin support parameters, and more specifically, to systems and methods for manipulating time blocks for insulin infusion delivery on a hand-held diabetes management device.

BACKGROUND

The statements in this section merely provide background information related to the present disclosure and may not constitute prior art.

Diabetes mellitus, often referred to as diabetes, is a chronic condition in which a person has elevated blood glucose levels that result from defects in the body's ability to produce and/or use insulin. There are three main types of diabetes. Type 1 diabetes usually strikes children and young adults, and may be autoimmune, genetic, and/or environmental. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. Its incidence is increasing rapidly, and it is estimated that between 2005 and 2030, the number of deaths from diabetes will double. In the United States, nearly 24 million Americans have diabetes with an estimated 25 percent of seniors age 60 and older being affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Diabetes is managed primarily by controlling the level of glucose in the bloodstream. This level is dynamic and complex, and is affected by multiple factors including the amount and type of food consumed, and the amount of insulin (which mediates transport of glucose across cell membranes) in the blood. Blood glucose levels are also sensitive to exercise, sleep, stress, smoking, travel, illness, menses, and other psychological and lifestyle factors unique to individual patients. The dynamic nature of blood glucose and insulin, and all other factors affecting blood glucose, often require a person with diabetes to forecast blood glucose levels. Therefore, therapy in the form of insulin or oral medications, or both, can be timed to maintain blood glucose levels in an appropriate range.

There is a need for a patient to be able to manage, manipulate and control the desired range of blood glucose levels over a period of time through a hand-held device in an efficient manner to improve the care and health of a person with diabetes, so the person with diabetes can lead a full life and reduce the risk of complications from diabetes.

SUMMARY

Provided is a system for modifying insulin therapy support parameters such as a start time of day data value, an end time of day data value, a lower blood glucose target data value, an upper blood glucose target data value, a high blood glucose warning data value and a low blood glucose warning data value on a hand-held diabetes management device. The system can include a graphical user interface module that creates a graphical user interface having a plurality of bar structures positionable on or between a first line that graphically indicates an upper boundary limit and a second line that graphically indicates a lower boundary limit. Each of the plurality of bar structures can have a first side that graphically indicates a start time of a time window opposite a second side that graphically indicates an end time of the time window and a third side that graphically indicates a start value for a range of values opposite a fourth side that graphically indicates an end value for the range of values. The first side, the second side, the third side and the fourth side of each of the plurality of bar structures, the first line and the second line can be adjustable by a user input. The plurality of bar structures can be governed by a set of constraints that confine each of the plurality of bar structures to an area defined by the first line and the second line and to a unique time window.

The system can also include a data store for storing at least the start time of day data value, the end time of day data value, the lower blood glucose target data value, the upper blood glucose target data value, the high blood glucose warning data value and the low blood glucose warning data value. The system can further include a data mapping module that maps for each of the plurality of bar structures on the graphical user interface the start time of day data value to a location of the first side, the end time of day data value to a location of the second side, the lower blood glucose target data value to a location of the third side and the upper blood glucose target data value to a location of the fourth side and stores the start time of day data value, end time of day data value, lower blood glucose target data value and upper blood glucose target data value in the data store. The data mapping module can also map the high blood glucose warning data value to a location of the first line and map the low blood glucose warning data value to a location of the second line. The data mapping module can store the high blood glucose warning data value and the low blood glucose warning data value in the data store.

Further provided is a system for modifying insulin therapy support parameters such as a start time of day data value, an end time of day data value, a lower blood glucose target data value, an upper blood glucose target data value, a high blood glucose warning data value and a low blood glucose warning data value on a hand-held diabetes management device. The system can include a graphical user interface module that creates a graphical user interface illustrating a bar chart having a plurality of bar structures, an x-axis graphically illustrating a time of day and a y-axis graphically illustrating a blood glucose level. The plurality of bar structures can be positionable on the bar chart, and each of the plurality of bar structures can have a first side that graphically indicates a start time of day opposite a second side that graphically indicates an end time of day and a third side that graphically indicates a lower target value for a blood glucose level opposite a fourth side that graphically indicates an upper target value for the blood glucose level. The first side, the second side, the third side and the fourth side of each of the plurality of bar structures can be adjustable by a user input. The third side of at least one of the plurality of bar structures can be spaced apart from the x-axis.

The system can also include a data store for storing at least the start time of day data value, the end time of day data value, the lower blood glucose target data value and the upper blood glucose target data value. The system can include a data mapping module that maps for each of the plurality of bar structures on the graphical user interface the start time of day data value to a location of the first side, the end time of day data value to a location of the second side, the lower blood glucose target data value to a location of the third side and the upper blood glucose target data value to a location of the fourth side and stores the start time of day data value, end time of day data value, lower blood glucose target data value and upper blood glucose target data value in the data store. The data mapping module can output the start time of day data value, end time of day data value, lower blood glucose target data value and upper blood glucose target data value to the hand-held diabetes management device.

Further areas of applicability will become apparent from the description provided herein. It should be understood that the description and specific examples are intended for purposes of illustration only.

BRIEF DESCRIPTION OF THE DRAWINGS

The drawings described herein are for illustration purposes only.

DETAILED DESCRIPTION

Figure 1:
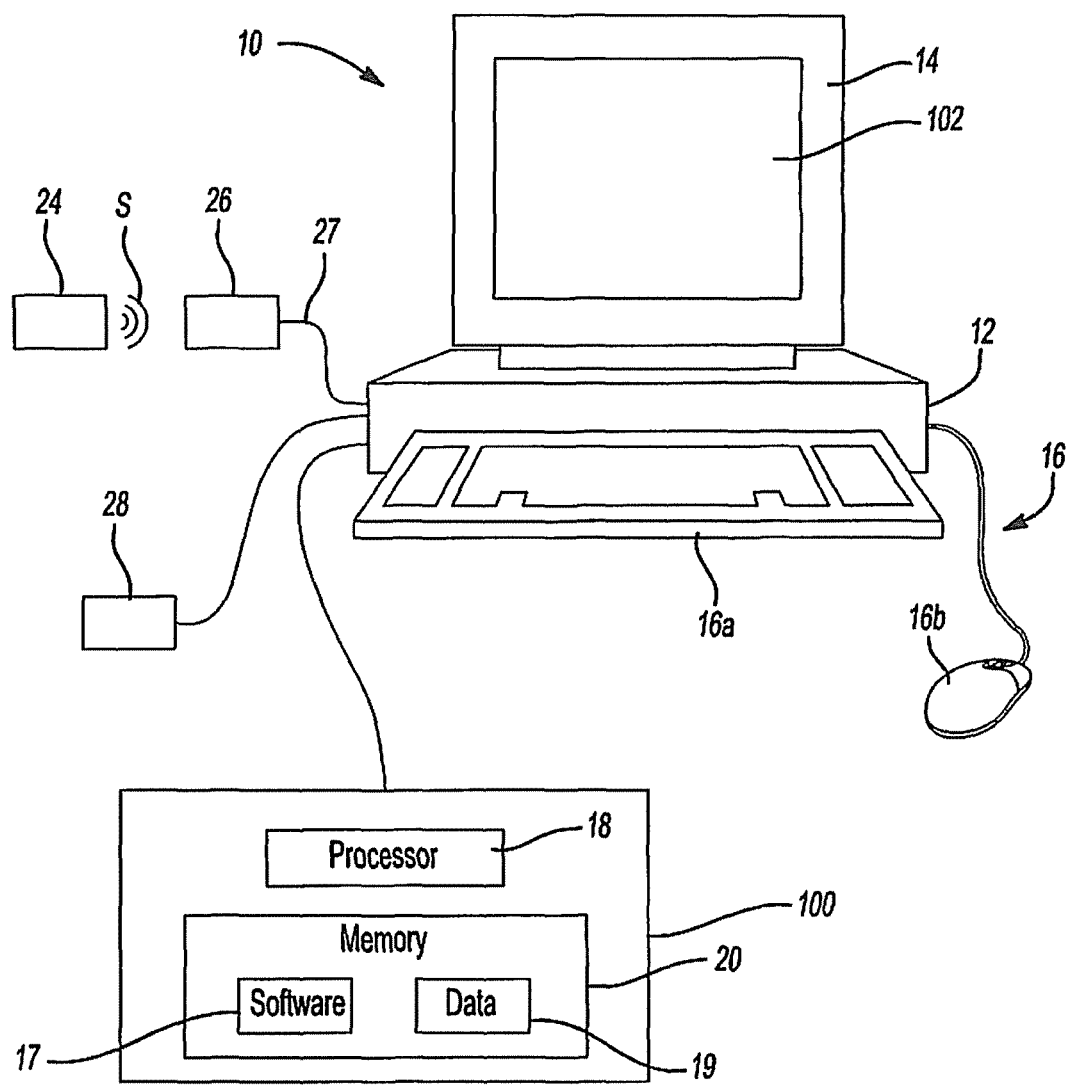
FIG. 1 is a schematic illustration of a computing system in communication with a hand-held diabetes device and a data storage device.

The following description is merely exemplary in nature. It should be understood that throughout the drawings, corresponding reference numerals indicate like or corresponding parts and features. As indicated above, the present teachings are directed toward providing a system and method for time block manipulation. It should be noted, however, that the present teachings could be applicable to any appropriate procedure in which it is desirable to modify a range of values over a period of time, such as a range of heart rate values over a period of time, for example. Further, as used herein, the term "module" can refer to a computer readable media that can be accessed by a computing device, an application specific integrated circuit (ASIC), an electronic circuit, a processor (shared, dedicated, or group) and memory that executes one or more software or firmware programs, a combinational logic circuit, and/or other suitable software, firmware programs or components that provide the described functionality.

It should be understood that although the concepts below are described as relating to diabetes management software systems for tracking and analyzing health data, such as, for example, the ACCU-CHEK® 360° product provided by Roche Diagnostics Corporation, the concepts apply to systems in other areas of healthcare. Moreover, the concepts described herein may also have applicability to apparatuses, methods, systems, and software in fields that are unrelated to healthcare. Furthermore, it should be understood that references in the present disclosure to devices, meters, monitors, or related items are intended to encompass any currently existing or later developed apparatus that includes some or all of the features attributed to the referred to apparatus, including but not limited to the ACCU-CHEK® Active, ACCU-CHEK® Aviva, ACCU-CHEK® Compact, ACCU-CHEK® Compact Plus, and ACCU-CHEK® Advantage, all commercially available from Roche Diagnostics Corporation or divisions thereof.

FIG. 1 is a diagram illustrating an exemplary embodiment of a computing system 10, some or all of the components of which can be used in conjunction with the teachings of the present disclosure. The computing system 10 can include a variety of computer-readable media. The computer-readable media can be any available media that can be accessed by the computing system 10 and includes both volatile and non-volatile media, and removable and non-removable media. By way of example, and not limitation, the computer-readable media can comprise computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the computing system 10. The computer-readable media may be accessed directly or through a network such as the Internet.

In one example, the computing system 10 comprises a system unit 12 and a display device 14. As illustrated, the display device 14 can comprise a computer video screen or monitor. The computing system 10 can also include at least one user input device 16. The system unit 12 includes, as shown in an exploded view at 100, a processor 18, and memory 20 that includes software 17 and data 19.

In this example, the at least one user input device 16 comprises a keyboard 16a and a pointing device 16b. It should be understood, however, that the at least one user input device 16 can comprise any suitable device to enable a user to interface with the computing system 10, such as a touchpad, touch pen, touch screen, keyboard, mouse, joystick, trackball, wireless mouse, or a combination thereof. Furthermore, while the computing system 10 is described and illustrated herein as comprising the system unit 12 with the display device 14, the computing system 10 could comprise a touchpad or tablet computing device, and further, that the computing system 10 could be integrated within or be part of a hand-held diabetes management device.

As will be discussed with regard to FIGS. 2 and 9-22, the computing system 10 can generate a plurality of graphical user interfaces 102 for display on the display 14. An exemplary user interface 102 can comprise at least one or a plurality of interactive screens that can be displayed on the display device 14. The user interface 102 can enable the user to manipulate or manage insulin therapy support parameters, such as time blocks and bolus advice settings, and save the parameters on a hand-held diabetes management device 24.

In this regard, the computing system 10 can provide information to, and receive information from, the hand-held diabetes management device 24. In one example, the hand-held diabetes management device 24 can comprise a hand-held glucose monitor; however, it should be understood that the teachings of the present disclosure also apply to devices such as a programmable insulin pump, or other such devices known or hereafter developed. In FIG. 1, the computing system 10 can be coupled to a communication media or dongle 26, which can be attached to the computing system 10 using a cable 27. The dongle 26 is configured to establish logical communication with the hand-held diabetes management device 24. For example, the dongle 26 can be a modulated signal transceiver that communicates with the hand-held diabetes management device 24 by transmitting and receiving a modulated radio-frequency (RF) signal S. In another exemplary embodiment, the computing system 10 and the hand-held diabetes management device 24 include ports configured to establish a physical connection. By way of example, the dongle 26 may include wired media such as a wired network or direct wired connection, and wireless media such as acoustic, RF, infrared and other wireless media. For example, the dongle 26 can include an infrared port for communication with a corresponding infrared port of the hand-held diabetes management device 24.

In addition, with continued reference to FIG. 1, the computing system 10 can include a data storage device 28. The data storage device 28 can comprise at least one of RAM, ROM, EEPROM, flash memory or other memory technology, CD-ROM, DVD or other optical disk storage, magnetic cassettes, magnetic tape, magnetic disk storage or other magnetic storage devices, or any other medium which can be used to store computer-readable instructions, software, data structures, program modules and other data and which can be accessed by and written to by the computing system 10. Thus, the data storage device 28 can be integral with the system unit 12 or can be in communication with the computing system 10 through a suitable connection. For example, the data storage device 28 can be accessed via a physical connection or a wireless connection, such as a wired network or direct wired connection, and wireless media such as acoustic, RF, infrared, and other wireless media. In one example, as illustrated, the computing system 10 and the data storage device 28 may include ports configured to establish a physical connection.

Figure 2:
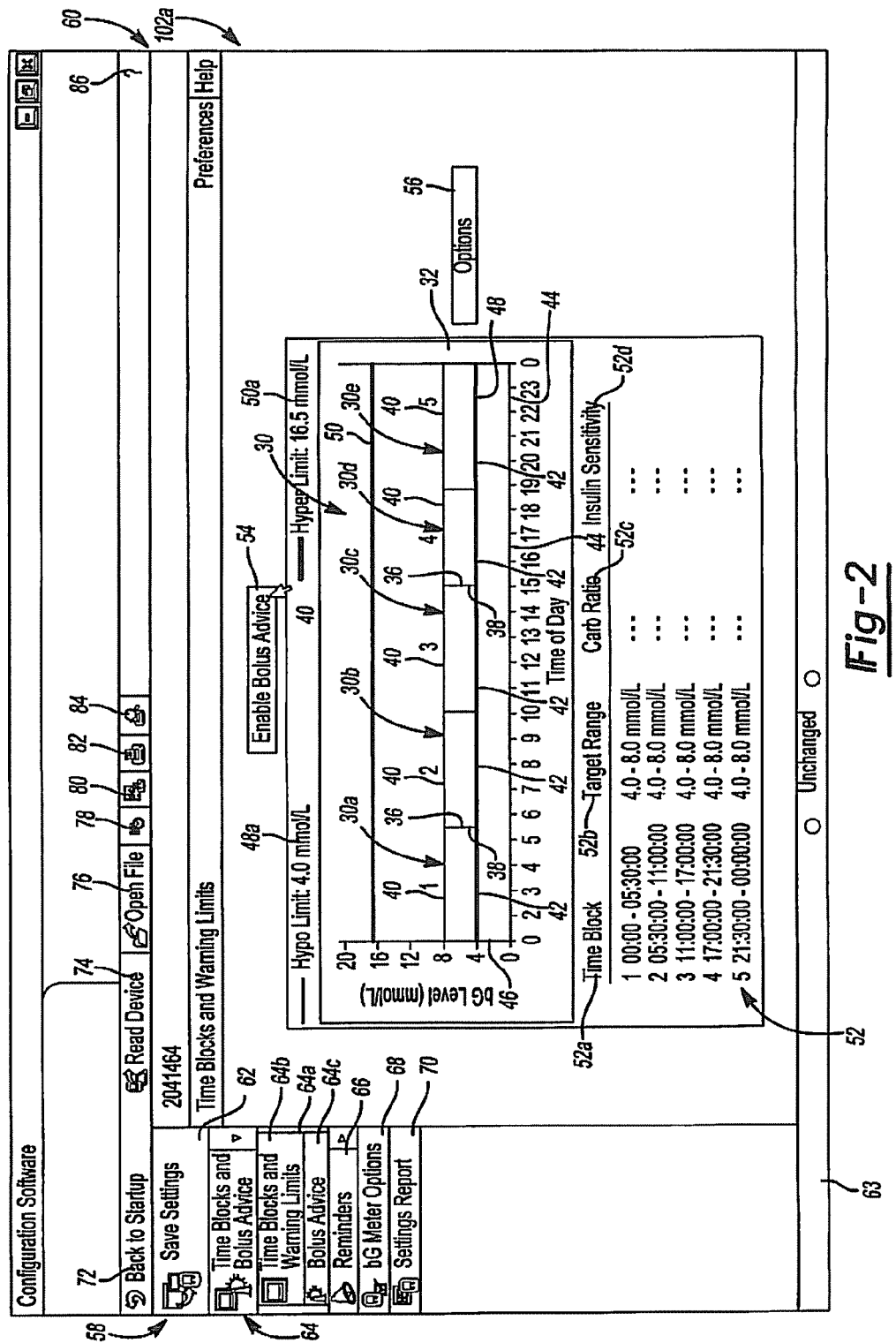
FIG. 2 illustrates an exemplary "Time Blocks and Warning Limits" user interface.

Briefly, with reference to FIG. 2, an exemplary user interface 102a, "Time Blocks and Warning Limits", of the plurality of user interfaces 102 is illustrated. The "Time Blocks and Warning Limits" user interface 102a can include at least one or a plurality of bar structures 30, which can be arranged as a bar chart 32. Software components for creating bar charts are commercially available, such as from Dundas Data Visualization Services, Inc. of Toronto, Ontario, Canada. It should be noted that while the "Time Blocks and Warning Limits" user interface 102a includes five bar structures 30a-30e, the "Time Blocks and Warning Limits" user interface 102a can include any number of bar structures 30, as will be discussed in greater detail herein.

Each of the plurality of bar structures 30 can include a first or left side 36 opposite a second or right side 38, and a third or top side 40 opposite a fourth or bottom side 42. Each of the plurality of bar structures 30 can graphically illustrate a range of values over a unique time window. In addition, the left side 36, right side 38, top side 40, and bottom side 42 can be manipulated by the user to select the range of values and unique time window, as will be discussed.

Generally, the "Time Blocks and Warning Limits" user interface 102a can also include an x-axis 44, a y-axis 46, a first or lower boundary line 48, and a second or upper boundary line 50. In one example, the x-axis 44 corresponds to a time of day in hours, and the y-axis 46 corresponds to a blood glucose (bG) level in millimoles per liter (mmol/liter). It should be noted that the illustrated scales for the x-axis 44 and the y-axis 46 are merely exemplary, and can use any suitable unit of measure for time and bG level, respectively. The location of the left side 36 of each bar of the plurality of bar structures 30a-30e corresponds to a start time of the unique time window for the bar and the right side 38 corresponds to an end time of the unique time window for the bar. The location of each bottom side 42 can correspond to a start value or lower target value of a range of bG levels, while the top side 40 can correspond to an end value or upper target value for the range of bG levels. Each of the plurality of bar structures 30 can be positioned on or between the lower boundary line 48 and the upper boundary line 50. In other words, the lower target value for the range of bG levels (the bottom side 42) need not be the same value as the lower boundary line 48.

The lower boundary line 48 can graphically represent a hypoglycemic warning limit for the user's bG level, and can comprise a horizontal line. As will be discussed, the user can use the at least one user input device 16 to move or position the lower boundary line 48 between the bottom side 42 having the lowest value and the x-axis 44 to enable the user to select a desired hypoglycemic warning limit based on the user's particular health needs. The particular bG level selected from the y-axis that corresponds to the lower boundary line 48 can be displayed as a "Hypo Limit" 48a on the "Time Blocks and Warning Limits" user interface 102a.

The upper boundary line 50 can graphically represent a hyperglycemic warning limit for the user's bG level, and can comprise a horizontal line. As will be discussed, the user can use the at least one user input device 16 to move or position the upper boundary line 50 above the lower boundary line 48 to enable the user to select a desired hyperglycemic warning limit based on the user's particular health needs. The particular bG level selected from the y-axis that corresponds to the upper boundary line 50 can be displayed as a "Hyper Limit" 50a on the "Time Blocks and Warning Limits" user interface 102a.

For purposes of illustration only, the bar structure 30a covers a time period beginning at the left side 36 of the bar structure 30a and ending at the right side 38 of the bar structure 30a. The bar structure 30a graphically illustrates upper and lower blood sugar limits applied during the time period. The upper limit is indicated by the top side 40 and the lower limit is indicated by the bottom side 42. In the depicted example, the lower limit (bottom side 42) is at the same level as the overall hypoglycemic limit ("Hypo Limit") 48. In various implementations, the lower limit (bottom side 42) can not be set lower than the overall hypoglycemic limit 48. Meanwhile, the upper limit (top side 40) is set below the overall hyperglycemic limit ("Hyper Limit") 50. In various implementations, the upper limit (top side 40) can not be set higher than the overall hyperglycemic limit 50.

In various implementations, the upper limit (top side 40) and the lower limit (bottom side 42) can be set individually for each of the bar structures 30. In addition, the beginning (left side 36) and end (right side 38) can be adjusted for each of the bar structures 30. Further, the number of bar structures 30 can be adjusted to change the number of time periods for which limit adjustments can be made.

The "Time Blocks and Warning Limits" user interface 102a can also include a summary section 52, a "Bolus Advice" button 54 and an "Options" button 56. The term "selector" and "button" as used herein can denote any appropriate user selection device that activates a feature on the user interface, such as a scroll bar, radio button, checkbox, button, drop-down menu, link or combinations thereof. The summary section 52 can be positioned adjacent to the bar chart 32, and can list the data associated with each of the bar structures 30a-30e in a tabular format. Exemplary headings for the summary section 52 include a "Time Block" heading 52a, a "Target Range" heading 52b, a "Carb Ratio" heading 52c and an "Insulin Sensitivity" heading 52d. As will be discussed in greater detail herein, the summary section 52 can be populated by the control module 100.

The "Time Block" heading 52a can comprise the start time of day value and the end time of day value for the particular time window, based on the location of the first side 36 and the third side 38 of each bar structure 30. The "Target Range" heading 52b can comprise a start value or lower target value for the range of bG levels and an end value or upper target value for the range of bG values based on the location of the bottom side 42 and the top side 40 of each of the bar structures 30.

Each of the "Carb Ratio" heading 52c and the "Insulin Sensitivity" heading 52d can be populated when the "Bolus Advice" button 54 is selected, as will be discussed in greater detail herein. If populated, the "Carb Ratio" heading 52c can comprise a user specific ratio of a number of units of insulin needed per a particular number of grams of carbohydrates for the time window and range of bG levels associated with each bar structure 30. The "Insulin Sensitivity" heading 52d can comprise a user-specific ratio of a number of units of insulin needed to affect a particular numeric change in the user's bG level for the period of time associated with the particular bar structure 30.

The "Bolus Advice" button 54 can enable the user to select whether to enable bolus advice data for each of the bar structures 30. The "Bolus Advice" button 54 can be positioned adjacent to or above the bar chart 32. As will be discussed herein, bolus advice data can comprise recommendations for the user if the value of the user's bG level falls outside of the range of bG levels identified for the respective bar structure 30 based on the carb ratio data and insulin sensitivity data associated with the particular bar structure 30. If the "Bolus Advice" button 54 is disabled, the "Bolus Advice" button 54 can display "Enable Bolus Advice." If the "Bolus Advice" button 54 is enabled, then the "Bolus Advice" button 54 can instead display "Disable Bolus Advice." In addition, if the "Bolus Advice" button 54 is enabled, then the control module 100 can display various bolus advice set-up user interfaces, as will be discussed further herein with reference to FIGS. 14-18.

The selection of the "Options" button 56 can cause the control module 100 to generate a "Time Blocks" user interface 102r that allows the user to manipulate each of the first side 36, second side 38, top side 40 and bottom side 42 of the bar structures 30, add or remove bar structures 30, and adjust the position of the lower boundary line 48 and the upper boundary line 50, as will be discussed further herein with regard to FIG. 21. The "Options" button 56 can be positioned generally adjacent to or to the side of the bar chart 32.

In addition, as will be discussed, various ones of the plurality of user interfaces 102 can each include a first or main menu 58, a second or sub menu 60 and a status indicator 61. Generally, the main menu 58 can include a "Save Settings" selector 62, a "Time Blocks and Bolus Advice" menu selector 64, a "Reminders" menu selector 66, a "bG Meter Options" selector 68 and a "Settings Report" selector 70. The main menu 58 can be positioned or anchored substantially vertically on a left side of each user interface 102, however, the main menu 58 could be positioned or anchored at any desired location on the user interface 102.

The "Save Settings" selector 62 can enable the user to save the data input to the user interface 102 to the hand-held diabetes management device 24 or to the data storage device 28. The user interface associated with the "Save Settings" selector 62 will be discussed with regard to FIGS. 19-20.

The "Time Blocks and Bolus Advice" menu selector 64 can provide a drop-down menu 64a, which can include a "Time Blocks and Warning Limits" button 64b and a "Bolus Advice" button 64c. The selection of the "Time Blocks and Warning Limits" button 64b can display the "Time Blocks and Warning Limits" user interface 102a illustrated in FIG. 2. The "Bolus Advice" button 64c can display a "Bolus Advice" user interface 102s, as will be discussed with regard to FIG. 22.

The features of the "Reminders" menu selector 66, the "bG Meter Options" selector 68 and the "Settings Report" selector 70 are beyond the scope of the present disclosure. Briefly, however, the "Reminders" menu selector 66 can display a user interface, which can enable the user to enter specific reminders that are associated with the management of the user's diabetes, such as a bG check reminder, a date reminder for a doctor's appointment, and alarm clocks that can be set to remind the user to perform specific tasks. The "bG Meter Options" selector 68 can display a user interface, which can enable the user to change or update settings specific to their hand-held diabetes management device 24, such as the language, date and time format, Bluetooth setting, unit settings (grams, units), maximum bolus dosage recommendation, sound and vibrate settings, and whether to lock the keys on the hand-held diabetes management device 24 (i.e. "keylock"). The "Settings Report" selector 70 can display a user interface, which can enable the user to view the current settings on their hand-held diabetes management device 24 and the changes made to the settings via user input to the user interface 102.

The sub menu 60 can be arranged generally horizontally on the user interface 102, and can be positioned above the main menu 58. It should be noted, however, that the sub menu 60 could be positioned or anchored at any desired location on the user interfaces 102. The sub menu 60 can include a "Back to Startup" button 72, a "Read Device" button 74, an "Open File" button 76, a "Set Date and Time" button 78, a "Create Pump/Meter Report" button 80, a "Print" button 82 and a "Print Preview" button 84. Additionally, the sub menu 60 can include a "Help" button 86.

The "Back to Startup" button 72, if selected, can display a "Startup" user interface 102b, as will be discussed with regard to FIG. 9. The "Read Device" button 74, if selected, can display a "Read From Device" user interface 102c, as will be discussed with regard to FIG. 10. The "Open File" button 76, if selected, can display an "Open File" user interface 102e, as will be discussed with regard to FIG. 12. The "Set Date and Time" button 78, if selected, can display a "Set Date and Time" user interface 102f, as will be discussed with regard to FIG. 13. The features of the "Create Pump/Meter Report" button 80 are beyond the scope of the present disclosure. Briefly, however, if selected, the "Create Pump/Meter Report" button 80 can generate a series of user interfaces that can enable the user to pair an insulin pump to the hand-held diabetes management device 24 and generate a report.

The "Print" button 82, if selected, can generate a user interface that can allow the user to print a configuration settings report, which can include at least information regarding the current configuration of the bar chart 32. The "Print Preview" button 84, if selected, can provide the user with a user interface, which can display a preview of the configuration settings report prior to printing.

The status indicator 63 can provide the user with a graphical illustration as to the status of the time block and bolus advice settings displayed on the user interfaces 102. In this regard, if the user has modified the user interfaces 102 via the at least one user input device 16, then the status indicator 63 can indicate "When ALL changes are complete, click "Save Settings to Device and/or File." If changes have not been made to the time block or bolus advice settings, then the status indicator 63 can display a suitable indicator such as "Unchanged." It should be noted that the statements displayed by the status indicator 63 are merely exemplary, as the status indicator 63 could display any other suitable phrase or instruction, and/or could display different colors, such as red and green, etc.

Figure 3:
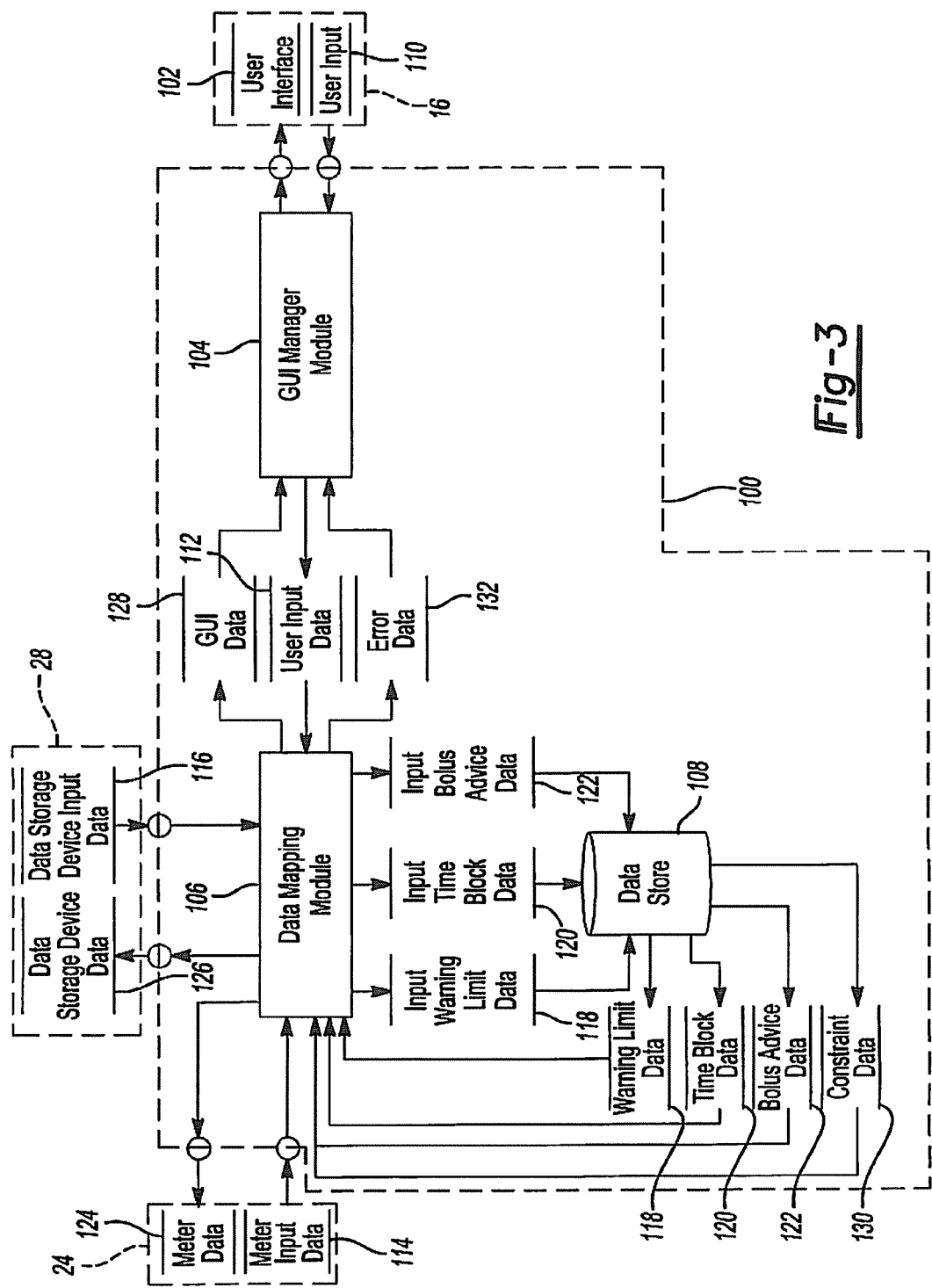
FIG. 3 is a dataflow diagram illustrating an exemplary control system performed by a control module.

Generally, with reference now to FIG. 3, a dataflow diagram illustrates various components of a user interface control system that can be embedded within the control module 100. The control module 100 can generate the plurality of user interfaces 102 for display on the display device 14. Various embodiments of the user interface control system according to the present disclosure can include any number of sub-modules embedded within the control module 100. The sub-modules shown may be combined and/or further partitioned to similarly generate the user interfaces 102. Further, the control module 100 can comprise one or more software modules embodied in non-transitory, machine readable code that runs on the processor 18. Inputs to the system can be received from the hand-held diabetes management device 24, the data storage device 28, the user input devices 16, or even received from other control modules (not shown) within the computing system 10, and/or determined by other sub-modules (not shown) within the control module 100 (not shown).

With reference to FIG. 3, the control module 100 can include a graphical user interface (GUI) manager module 104, a data mapping module 106 and a data store 108. The graphical user interface manager module 104 can generate the user interface 102 to enable a user to manipulate various insulin therapy support parameters, such as those graphically associated with the bar structures 30, lower boundary line 48, upper boundary line 50, along with the bolus advice data parameters, which can be saved to the hand-held diabetes management device 24 or the data storage device 28. The graphical user interface manager module 104 can receive as input user input 110, which can be received from the at least one user input device 16. The user input 110 can comprise an input to the user interface 102 from the at least one user input device 16 to adjust one or more of the left side 36, right side 38, top side 40 and/or bottom side 42 of the plurality of bar structures 30, a location for the lower boundary line 48, a location of the upper boundary line 50, a request to add a new bar structure 30, a carb ratio for a particular bar structure 30, an insulin sensitivity value for a particular bar structure 30, etc.

The graphical user interface manager module 104 can also receive graphical user interface data 128 and error data 132 as input from the data mapping module 106. The graphical user interface data 128 and error data 132 can each comprise instructions regarding the creation of the user interfaces 102, as will be discussed. The graphical user interface manager module 104 can set user input data 112, which comprises the user input 110, for the data mapping module 106, and can output the user interfaces 102 based on the graphical user interface data 128 and error data 132.

The data mapping module 106 can receive as input the user input data 112. The data mapping module 106 can also receive as input meter input data 114, data storage device input data 116 and constraint data 130. The meter input data 114 can comprise data input by the user to the hand-held diabetes management device 24, such as a hyperglycemic warning limit, a hypoglycemic warning limit, time blocks, carb ratios for a particular time block and/or insulin sensitivity for a particular time block. The meter input data 114 can be read from the hand-held diabetes management device 24, when the user selects to the "Read From Device" button 74 (FIG. 2).

The data storage device input data 116 can comprise data read from the data storage device 28, which can include a hyperglycemic warning limit, a hypoglycemic warning limit, time blocks, carb ratios for a particular time block and/or insulin sensitivity for a particular time block. The data storage device input data 116 can be read from the data storage device 28 when the user selects to the "Open from File" button 76 (FIG. 2).

The constraint data 130 can be received as input from the data store 108. The constraint data 130 can include one or more rules regarding the data values for the hyperglycemic warning limit, the hypoglycemic warning limit and the time blocks, which can be applied to constrain or limit the manipulation of the upper boundary line 48, lower boundary line 50 and bar structures 30 by the user input device 116. Exemplary constraint data 130 can include the limitation that each bar structure 30 is confined to a unique time window, such that adjacent bar structures 30 cannot overlap, that the upper boundary line 50 cannot be positioned below the lower boundary line 48, and that the bar structures 30 are to be positioned between the upper boundary line 50 and the lower boundary line 48. Additional constraints can include particular data value minimums for the lower boundary line 48 and the upper boundary line 50, a maximum number of bar structures 30, a minimum number of bar structures 30, etc.

Based on the user input data 112, the meter input data 114, the data storage device input data 116 and the constraint data 130, the data mapping module 106 can determine warning limit data 118, time block data 120, bolus advice data 122 and error data 132. The data mapping module 106 can determine the warning limit data 118 based on both the hypoglycemic warning limit and hyperglycemic warning limit received from the meter input data 114 or the data storage device input data 116. The warning limit data 118 can also comprise the location of the lower boundary line 48 and the upper boundary line 50 received from the user input data 112. For example, the data mapping module 106 can map or assign a hypoglycemic warning limit to the location of the lower boundary line 48 as received from the user input data 112. As a further example, the data mapping module 106 can map or assign the hyperglycemic warning limit to the location of the upper boundary line 50 as received from the user input data 112. The hyperglycemic warning limit and the hypoglycemic warning limit can be saved as warning limit data 118 by the data mapping module 106 in the data store 108.

The data mapping module 106 can determine the time block data 120 based on both the time blocks received from the meter input data 114 or the data storage device input data 116. The time block data 120 can also comprise the location of the plurality of bar structures 30 received from the user input data 112. For example, the data mapping module 106 can map or assign the start time of day to the location of the left side 36 of each of the bar structures 30 as received from the user input data 112. As a further example, the data mapping module 106 can map or assign the end time of day to the location of the right side 38 of each of the bar structures 30 as received from the user input data 112, and the data mapping module 106 can map or assign the low bG level for a range of bG levels to the location of the bottom side 42 of each of the bar structures 30 as received from the user input data 112. Further, the data mapping module 106 can map or assign the high bG level for the range of bG levels to the location of the top side 40 of each of the bar structures 30 as received from the user input data 112.

Thus, the data mapping module 106 can generate time block data 120 based on the locations of the bar structures 30 on the user interface 102. In general, the time block data 120 can comprise a start time of day data value, an end time of day data value, a low bG level data value and a high bG level data value. In other words, the time block data 120 can comprise a plurality of unique time windows, each of which can have a specified range of bG levels during the respective time window. The start time of day data value, the end time of day data value, the low bG level data value and the high bG level data value can be saved by the data mapping module 106 as time block data 120 in the data store 108.

The data mapping module 106 can determine the bolus advice data 122 based on the bolus advice received from the meter input data 114 or the data storage device input data 116. The bolus advice data 122 can also comprise the carb ratio data and the insulin sensitivity data for each of the bar structures 30 as received by the user input data 112. The carb ratio data and the insulin sensitivity data can be saved by the data mapping module 106 as bolus advice data 122 in the data store 108.

The data mapping module 106 can determine the error data 132 based on the user input data 112 received as input and the constraint data 130. In this regard, if the user input data 112 includes requests to manipulate the user interface 102 that conflict with the constraint data 130, then the data mapping module 106 can set error data 132 for the graphical user interface manager module 104. The graphical user interface manager module 104 can then display the error data 132 on the user interface 102.

The data mapping module 106 can retrieve the stored warning limit data 118, the time block data 120 and the bolus advice data 122 from the data store 108 and can output the stored warning limit data 118, the time block data 120 and the bolus advice data 122 as meter data 124 for the hand-held diabetes management device 24 based on the user input data 112. In this regard, the data mapping module 106 can output the meter data 124 in request to the user selecting the "Save Settings" button 62 from the sub menu 60 (FIG. 2).

In addition, the data mapping module 106 can retrieve the stored warning limit data 118, the time block data 120 and the bolus advice data 122 from the data store 108 and can output the stored warning limit data 118, the time block data 120 and the bolus advice data 122 as data storage device data 126 for the data storage device 28 based on the user input data 112. In this regard, the data mapping module 106 can output the data storage device data 126 in request to the user selecting the "Save Settings" button 62 from the sub menu 60 (FIG. 2).

The data mapping module 106 can retrieve the stored warning limit data 118, the time block data 120 and the bolus advice data 122 from the data store 108 and can set the stored warning limit data 118, the time block data 120 and the bolus advice data 122 as graphical user interface data 128 for the graphical user interface module based on the user input data 112. The graphical user interface data 128 can be displayed as the summary data 52, or could be displayed initially on the "Time Blocks and Warning Limits" screen 102a (FIG. 2). In this regard, the data mapping module 106 can set the graphical user interface data 128 for the graphical user interface module 102 in response to the user selecting the "Open File" button 76 from the sub menu 60 (FIG. 2).

The data store 108 can comprise one or more data storage devices, which can be at least one of a RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules and other data associated with the control module 100. The data store 108 can store the warning limit data 118, the time block data 120 and the bolus advice data 122 received from the data mapping module 106, and can also set the stored warning limit data 118, the time block data 120 and the bolus advice data 122 for retrieval by the data mapping module 106. The data store 108 can also store the constraint data 130, which can be retrieved by the data mapping module 106.

Figure 4:
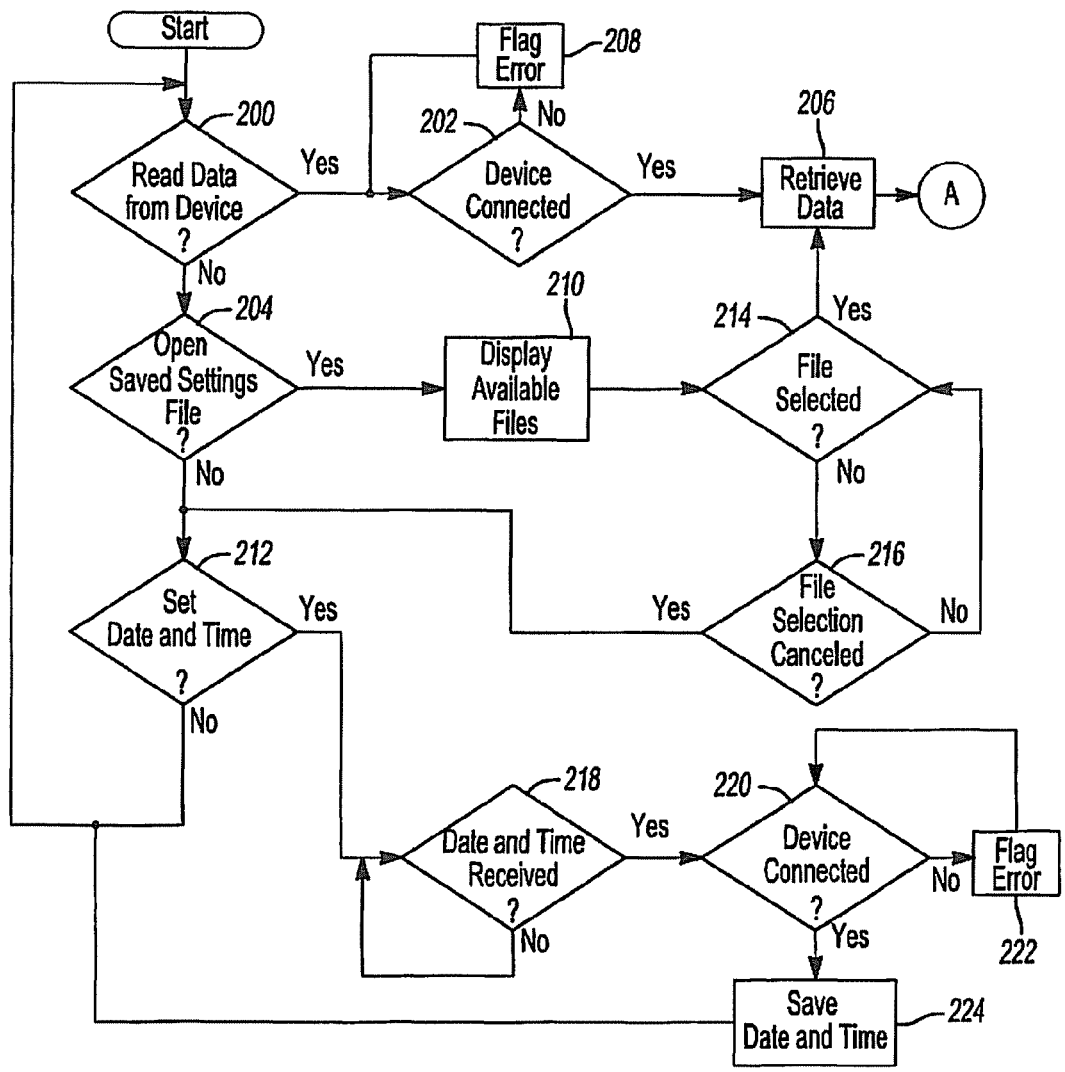
FIG. 4 is a flowchart illustrating a method performed by the control module.

With reference now to FIG. 4, a flowchart diagram illustrates an exemplary method performed by the control module 100. It should be noted that the flowchart diagram described herein with regard to FIGS. 4-7 is merely exemplary, as the control module 100 could generate the plurality of user interfaces 102 in any desired or user requested sequence. With continued reference to FIG. 4, at decision block 200 the method can determine if a request to retrieve data from the hand-held diabetes device 24 has been received. If a request to retrieve data from the hand-held diabetes device 24 has been received, then the method can go to decision block 202. Otherwise, the method can go to decision block 204.

At decision block 202, the method can determine if the hand-held diabetes device 24 is connected so as to be in communication with the computing system 10. If the hand-held diabetes device 24 is connected, then the method can go to block 206. Otherwise, the method goes to block 208 and flags an error. At block 206 the method can retrieve the meter input data 114. Then, the method can go to A on FIG. 5.

With continued reference to FIG. 4, at decision block 204 the method can determine if a request has been received to open a saved data file, such as a data file stored on the data storage device 28. If a request has been received to open a saved data file, the method can go to block 210. Otherwise, the method can go to decision block 212. At block 210, the method can display an "Open a Settings File" user interface 102e (FIG. 13), which can list available data files. Then, the method can go to decision block 214.

At decision block 214 the method can determine if a data file has been selected. If a data file has been selected, the method goes to block 206. Otherwise, the method goes to decision block 216. At decision block 216, the method determines if the data file selection has been cancelled. If the file selection has been cancelled, then the method can go to decision block 212. Otherwise, the method loops to decision block 214.

At decision block 212, the method can determine if a request has been received to set the date and time on the hand-held diabetes device 24. If no request has been received, the method can loop to decision block 200. Otherwise, the method can go to decision block 218. At decision block 218, the method can determine if the date and time have been entered via the at least one user input device 16. Alternatively, the input from the at least one user input device 16 can comprise a request to set the date and time to that of the computing system 10. If the date and time have been received, then the method can go to decision block 220. Otherwise, the method can loop until user input 110 is received.

At decision block 220, the method can determine if the hand-held diabetes device 24 is connected so as to be in communication with the computing system 10. If the hand-held diabetes device 24 is not connected, the method can go to block 222. At block 222, the method can flag an error and then loop to decision block 220. If the hand-held diabetes device 24 is connected so as to be in communication with the computing system 10, then the method can go to block 224. At block 224, the method can save the date and time to the hand-held diabetes device 24. Then, the method can loop to decision block 200.

Figure 5:
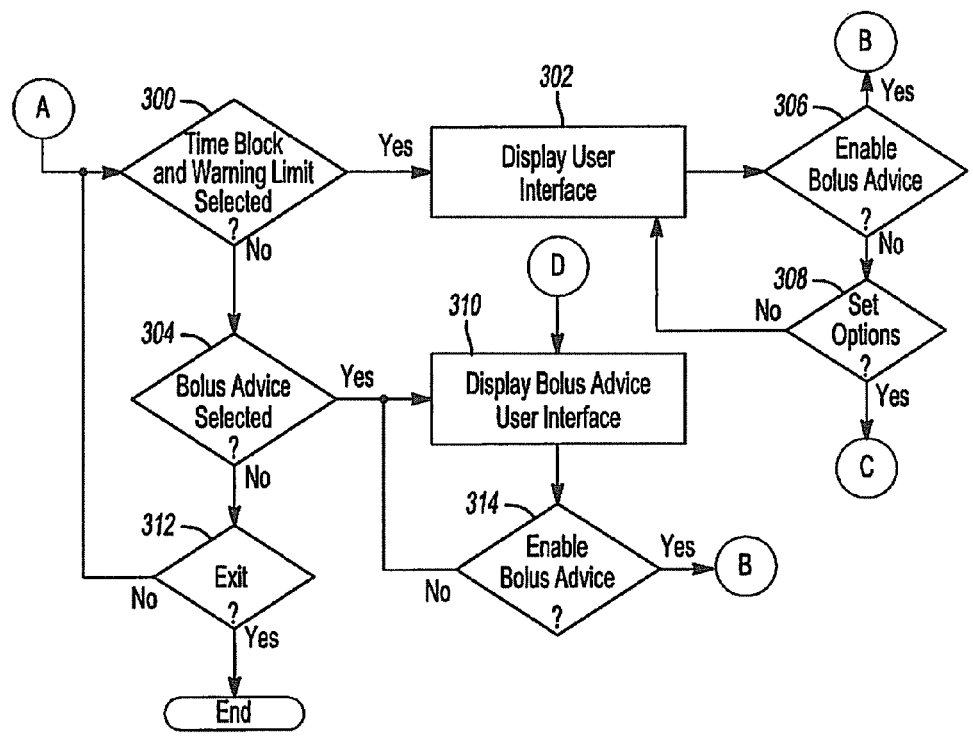
FIG. 5 is a continuation of the flowchart of FIG. 4 at A.

With reference to FIG. 5, starting at A, the method can go to decision block 300. At decision block 300, the method can determine if the "Time Blocks and Warning Limits" button 64b has been selected. If the "Time Blocks and Warning Limits" button 64b is selected, then the method can go to block 302. Otherwise, the method can go to decision block 304.

At block 302, the method can display the "Time Blocks and Warning Limits" user interface 102a. Then, the method can go to decision block 306. At decision block 306, the method can determine if the "Bolus Advice" button 64c has been selected. If the "Bolus Advice" button 64c has been selected, then the method can go to B on FIG. 6. Otherwise, the method can go to decision block 308. At decision block 308, the method can determine if the "Options" button 56 has been selected. If the "Options" button 56 has not been selected, then the method can loop to block 302. Otherwise, the method goes to C on FIG. 6.

Figure 22:
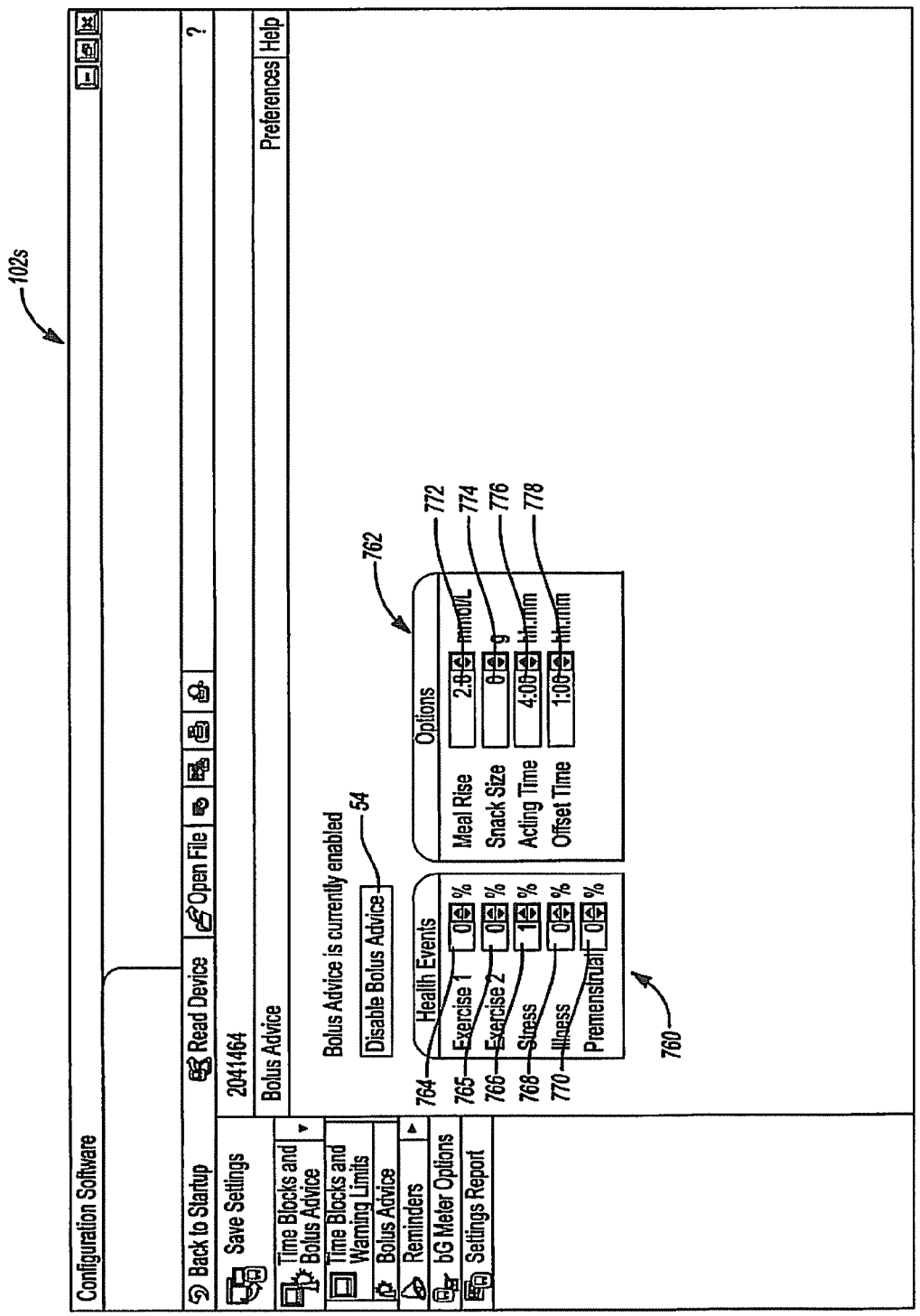
FIG. 22 illustrates an exemplary "Bolus Advice" user interface.

With reference to FIG. 5, at decision block 304, the method can determine if the "Bolus Advice" button 64c has been selected. If the "Bolus Advice" button 64c has been selected, the method can go to block 310. Otherwise, the method goes to block 312. At block 310, the method can display the "Bolus Advice" user interface 102s (FIG. 22). Then, the method can go to decision block 314.

At decision block 314, the method can determine whether the "Bolus Advice" button 54 has been selected. If the "Bolus Advice" button 54 has been selected, then the method can go to B on FIG. 6. Otherwise, the method can loop to block 310. At decision block 312, the method can determine if an exit request has been received. If a request to exit has been received the method can end. Otherwise, the method can loop to decision block 300.

Figure 6:
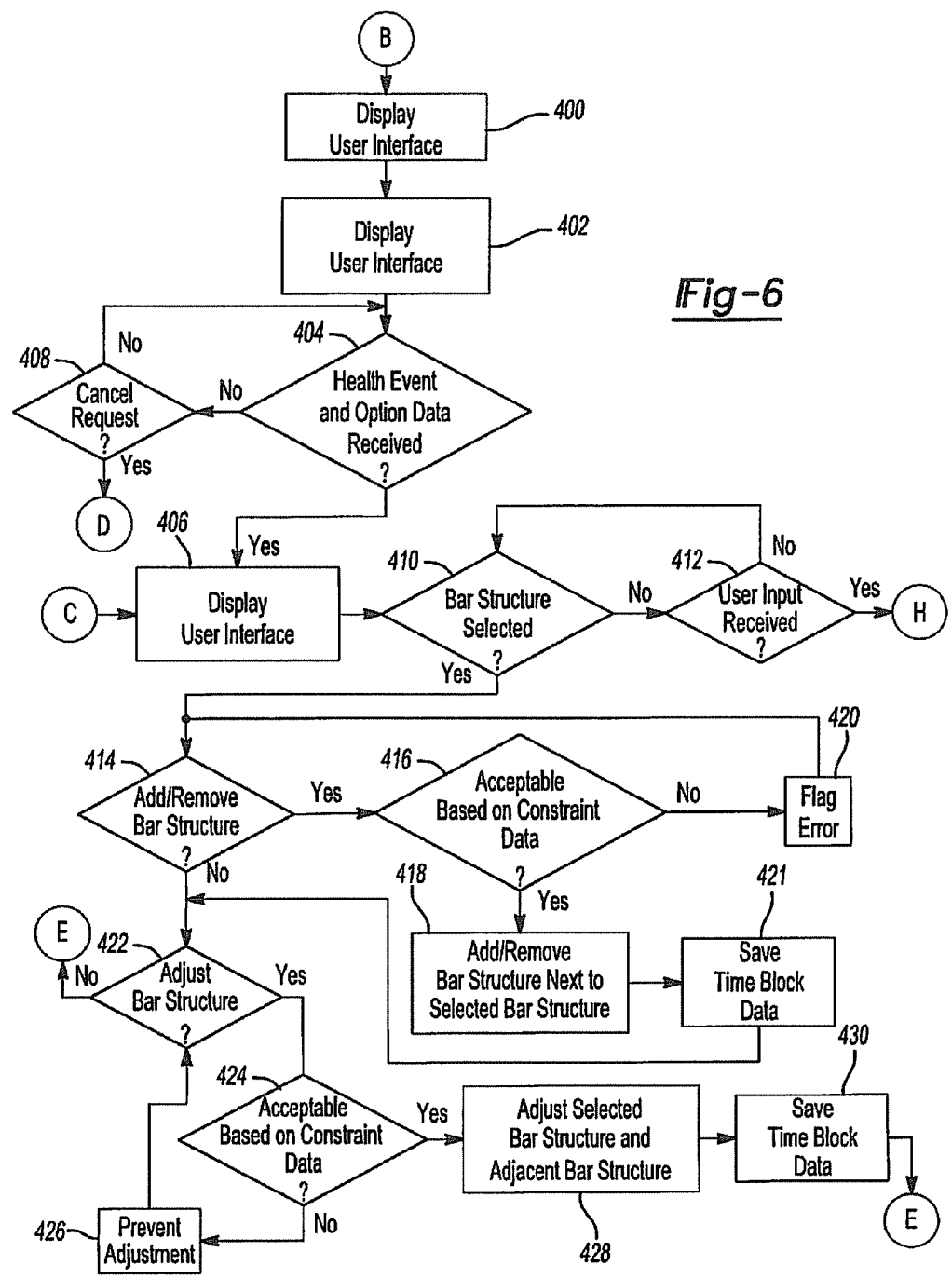
FIG. 6 is a continuation of the flowchart of FIG. 5 at B.
Figure 14:
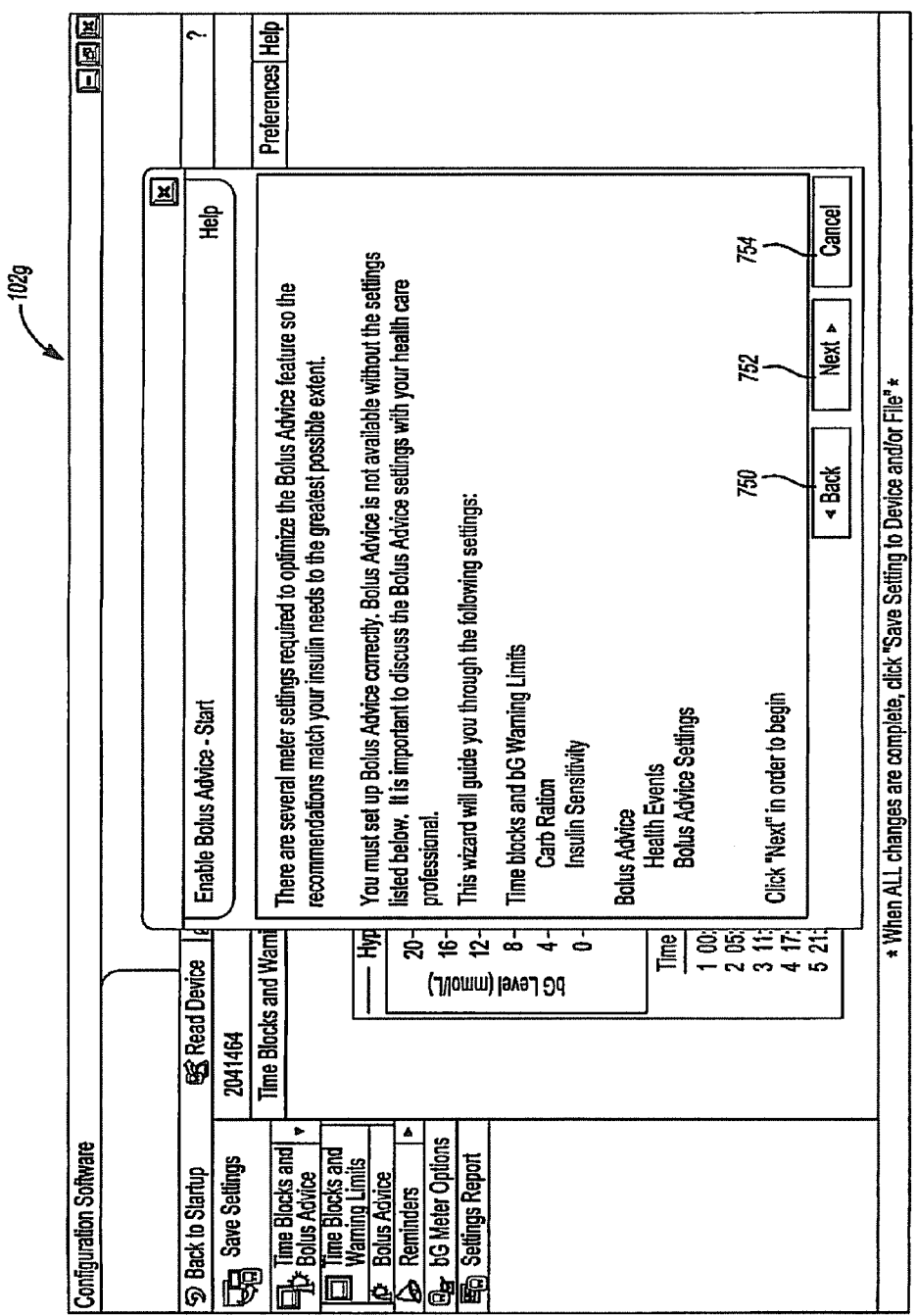
FIG. 14 illustrates an exemplary "Enable Bolus Advice-Start" user interface.
Figure 15:
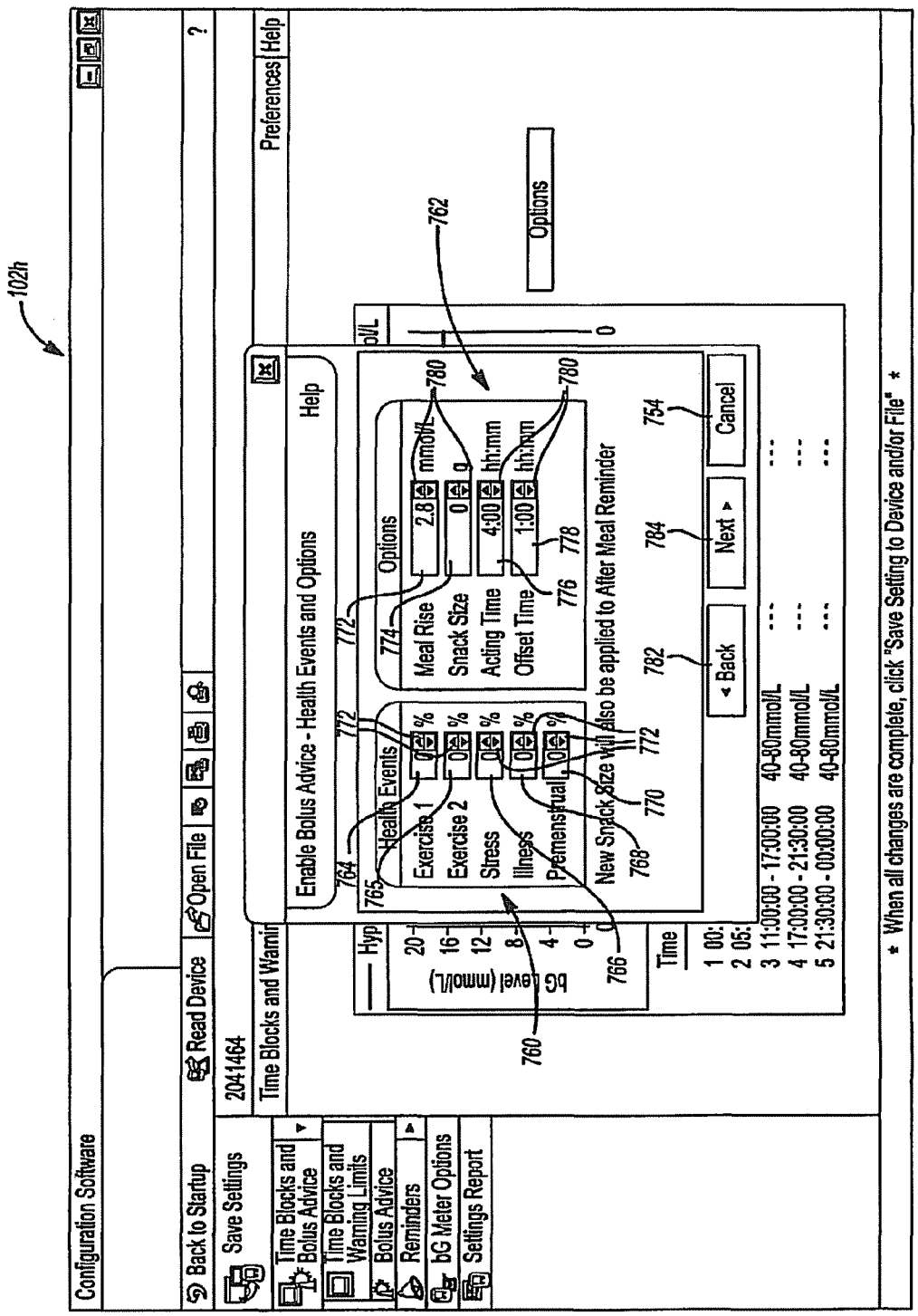
FIG. 15 illustrates an exemplary "Enable Bolus Advice-Health Events and Options" user interface.

With reference to FIG. 6, starting at B, the method can go to block 400. At block 400, the method can display an "Enable Bolus Advice-Start" user interface 102g (FIG. 14). Then, at block 402, the method can display a "Enable Bolus Advice-Health Events and Options" user interface 102h (FIG. 15). At decision block 404, the method can determine if health event and options data has been received via the at least one user input device 16. If the health event and option data has been received, then the method can go to block 406. Otherwise, the method goes to decision block 408.

At decision block 408, the method determines if a cancel request has been received through the at least one user input device 16. If the cancel request has been received, then the method goes to D on FIG. 5. If the cancel request has not been received, then method loops to decision block 404.

Figure 16A:
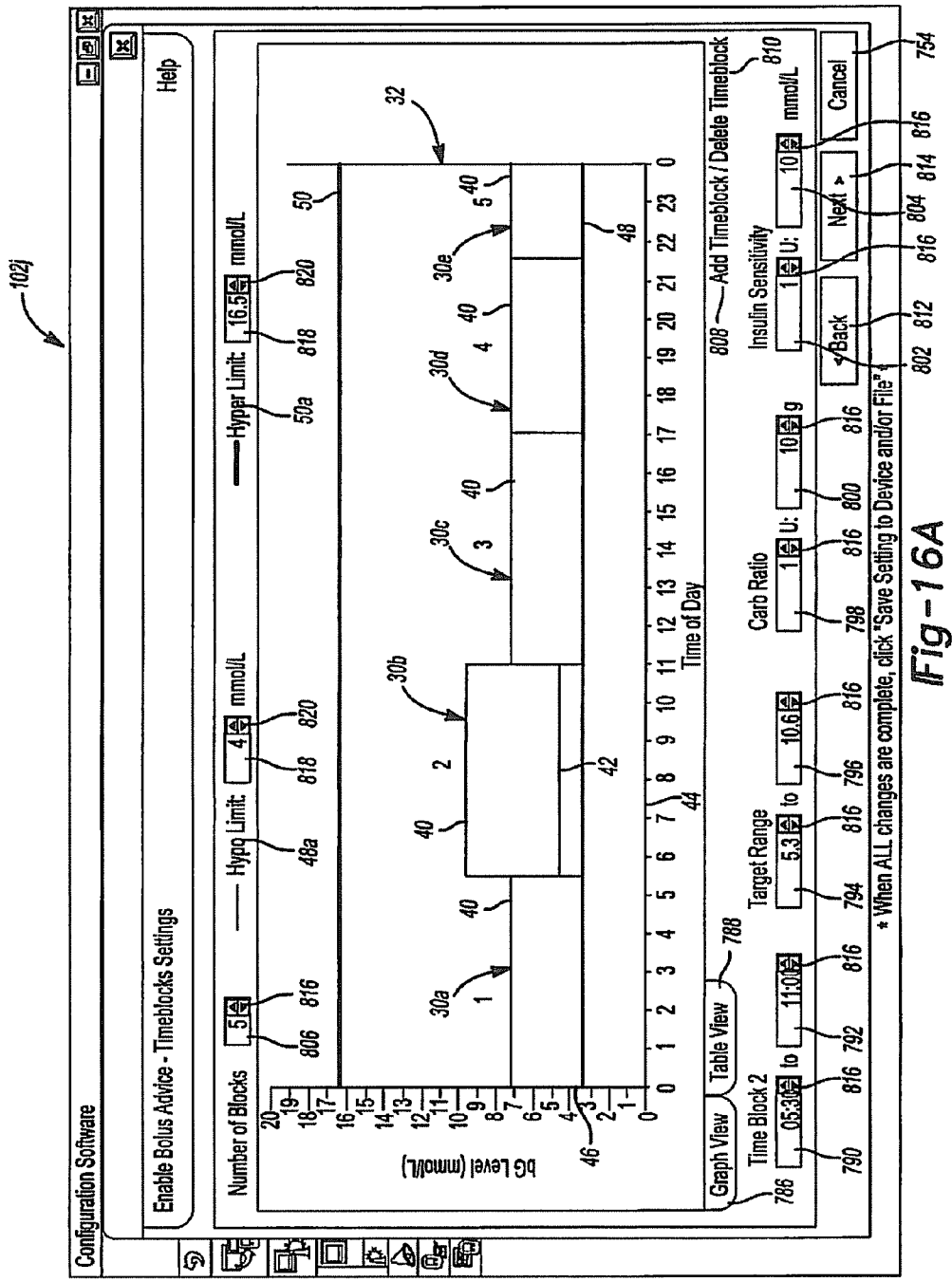
FIG. 16A illustrates an exemplary "Enable Bolus Advice-Timeblocks Settings" user interface.
Figure 16B:
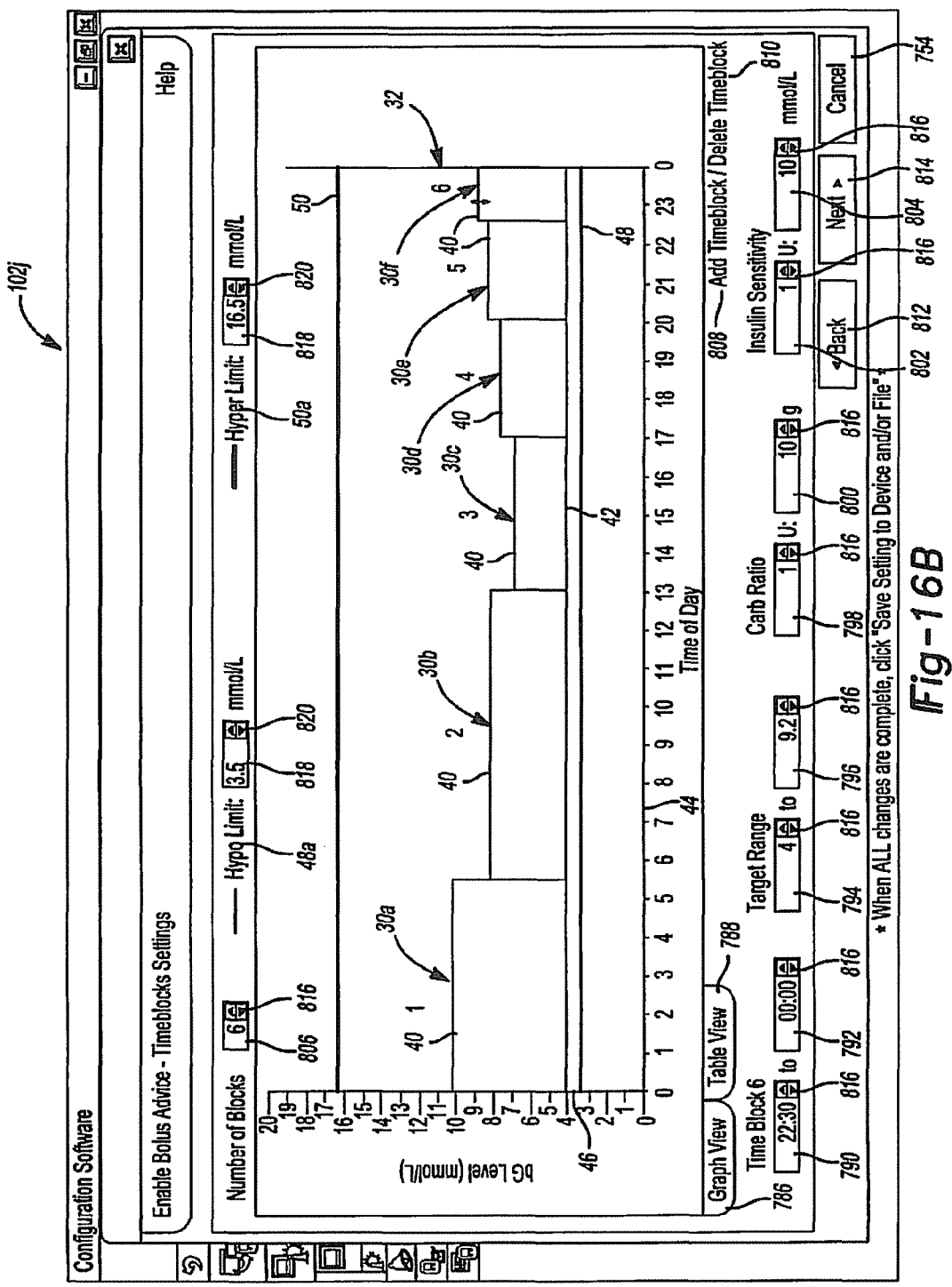
FIG. 16B illustrates the "Enable Bolus Advice-Timeblocks Settings" user interface of FIG. 16A in which the user interface illustrates an additional bar structure.
Figure 16C:
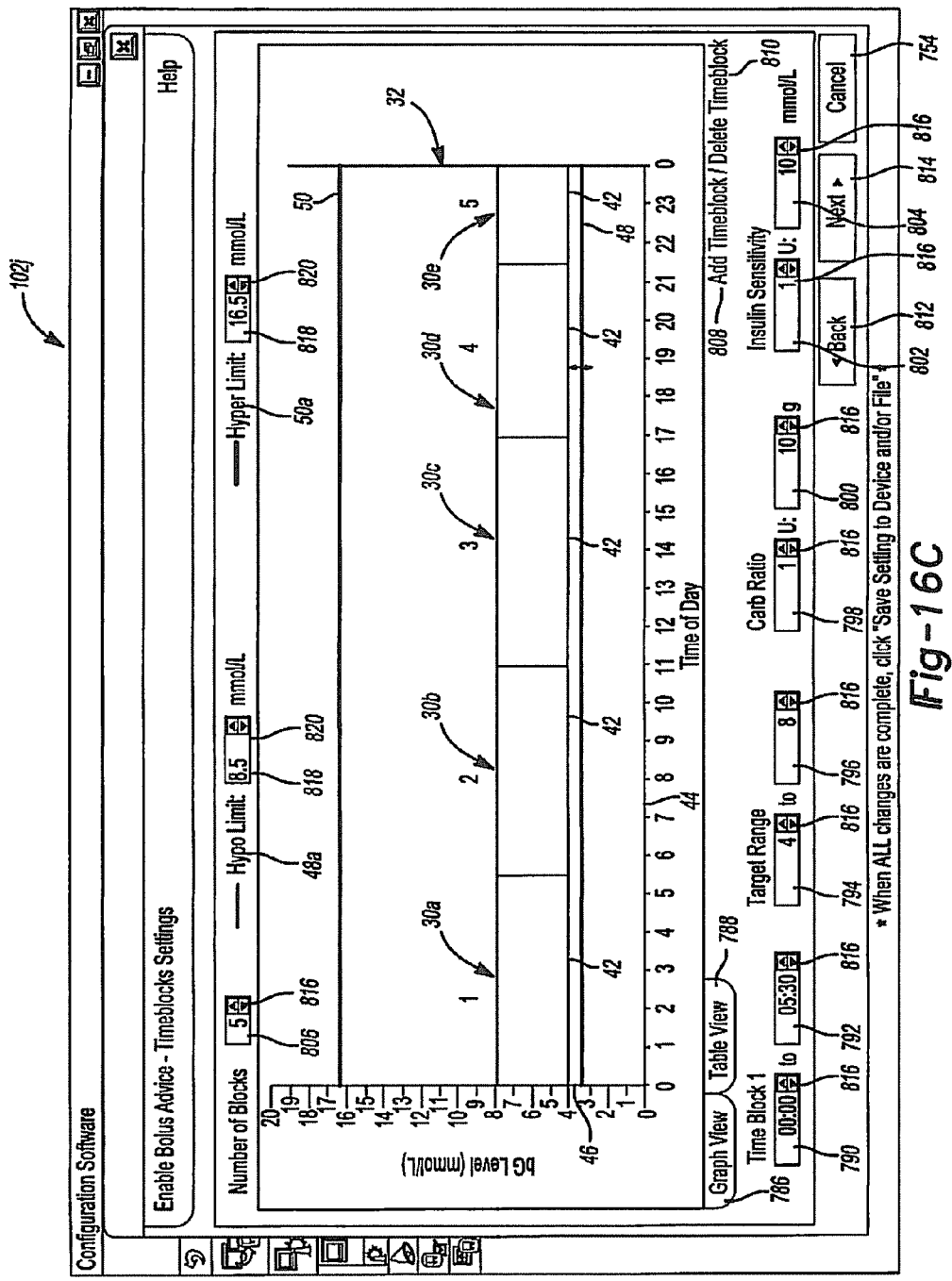
FIG. 16C illustrates the "Enable Bolus Advice-Timeblocks Settings" user interface of FIG. 16A in which the user interface illustrates moving a boundary line.

At block 406, the method can display an "Enable Bolus Advice-Timeblocks Settings" user interface 102j (FIGS. 16A-16C), then the method can go to decision block 410. At decision block 410, the method can determine if a particular bar structure 30 has been selected with the at least one user input device 16. If a bar structure has not been selected, then the method can go to decision block 412. At decision block 412, the method can determine if user input 110 has been received on the "Enable Bolus Advice-Timeblocks Settings" user interface 102j (FIGS. 16A-16C). If user input data 112 has been received, then the method can go to H on FIG. 7. Otherwise, the method can loop to decision block 410.

If a bar structure 30 has been selected at decision block 410, then the method can go to decision block 414. At decision block 414, the method can determine if the user input data 112 includes a request to add or remove the bar structure. If, at decision block 414, the user input data 112 includes a request to add or remove a bar structure 30, then the method can go to decision block 416. At decision block 416, the method can determine if the requested change in the number of bar structures 30 is acceptable based on the constraint data 130. If the requested change in the number of bar structures 30 is unacceptable based on the constraint data 130, then the method can go to block 418. Otherwise, the method can go to block 420. At block 420, the method can flag an error, and then loop to decision block 414.

If the change in the number of bar structures 30 is acceptable based on the constraint data 130, then at block 418 the method can either add a new bar structure 30 next to the selected bar structure 30 or can remove the selected bar structure 30 based on the user input data 112. Then, the method can go to block 421. At block 421, the method can save the locations of bar structures 30 as time block data 120. Then, the method can go to decision block 422.

At decision block 422, the method can determine if one of the left side 36, right side 38, top side 40 or bottom side 42 of the bar structures 30 has been adjusted via the at least one user input device 16. If one of the left side 36, right side 38, top side 40, or bottom side 42 has changed locations, then the method can go to decision block 424. At decision block 424, the method can determine if the adjustment to the side of the selected bar structure 30 is acceptable based on the constraint data 130. If the adjustment is not acceptable based on the constraint data 130, then at block 426 the method can prevent the adjustment of the one of the left side 36, right side 38, top side 40 or bottom side 42 of the selected bar structure 30. Then, the method can go to decision block 422. Otherwise, if the adjustment is acceptable, then the method can go to block 428.

At block 428, the method can adjust the selected bar structure 30 and the adjacent bar structure 30 if applicable. Then, the method can go to block 430. At block 430, the method can save the bar structure locations as time block data 120. Then, the method can go to E on FIG. 7. If at decision block 422, one of the left side 36, right side 38, top side 40 or bottom side 42 of the selected bar structure 30 the user has not been adjusted, then the method can also go to E on FIG. 7.

Figure 7:
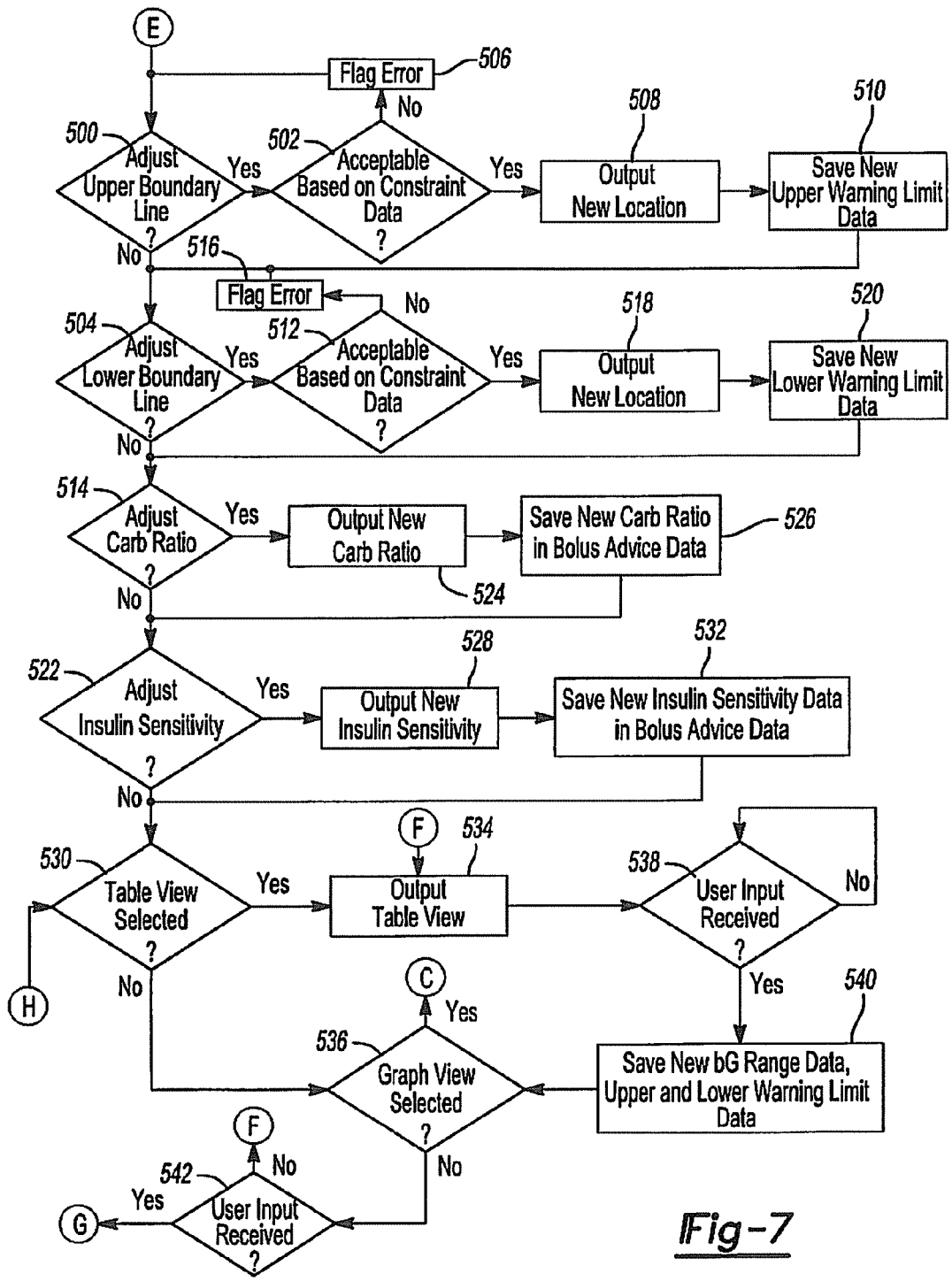
FIG. 7 is a continuation of the flowchart of FIG. 6 at E.

With reference to FIG. 7, starting at E, the method can go to decision block 500. At decision block 500, the method can determine if the upper boundary line 50 has been adjusted. If the upper boundary line 50 has been adjusted, then method can go to decision block 502. Otherwise, the method can go to decision block 504.

At decision block 502, the method can determine if the new location for the upper boundary line 50 is acceptable based on the constraint data 130. If the new location of the upper boundary line 50 is not acceptable, then the method can go to block 506. At block 506, the method can flag an error and then loop to decision block 500. If the new location for the upper boundary line 50 is acceptable, then at block 508 the method can display the new location for the upper boundary line 50 on the user interface along with the new "Hyper limit" data 50a. Then, the method can go to block 510. At block 510, the method can save the new location of the upper boundary line 50 as warning limit data 118. Then, the method can go to decision block 504.

At decision block 504, the method can determine if the location of the lower boundary line 48 has been adjusted. If the location of the lower boundary line 48 has been adjusted, then the method can go to decision block 512. Otherwise, the method can go to decision block 514. At decision block 512, the method can determine if the new location for the lower boundary line 48 is acceptable based on the constraint data 130. If the new location of the lower boundary line 48 is not acceptable, then at block 516 the method can flag an error before looping to decision block 504. If the new location for the lower boundary line 48 is acceptable, then the method can go to block 518.

At block 518, the method can display the lower boundary line 48 at the new location and can also display the new "Hypo Limit" data 48a associated with the new location of the lower boundary line 48. At block 520, the method can save the new location of the lower boundary line 48 as warning limit data 118. Then, the method can go to decision block 514.

At decision block 514, the method can determine if the carb ratio has been adjusted. If the carb ratio has not been adjusted, then the method can go to decision block 522. Otherwise, at block 524 the method can display a new carb ratio and can save the new carb ratio as bolus advice data 122 in the data store 108. Then, the method can go to decision block 522. At decision block 522, the method can determine if the insulin sensitivity has been adjusted. If the insulin sensitivity has been adjusted, then the method can go to block 528. Otherwise, the method can go to decision block 530. At block 528, the method can display the new insulin sensitivity. Then, the method can go to block 532. At block 532, the method can save the new insulin sensitivity data as bolus advice data 122.

Figure 17:
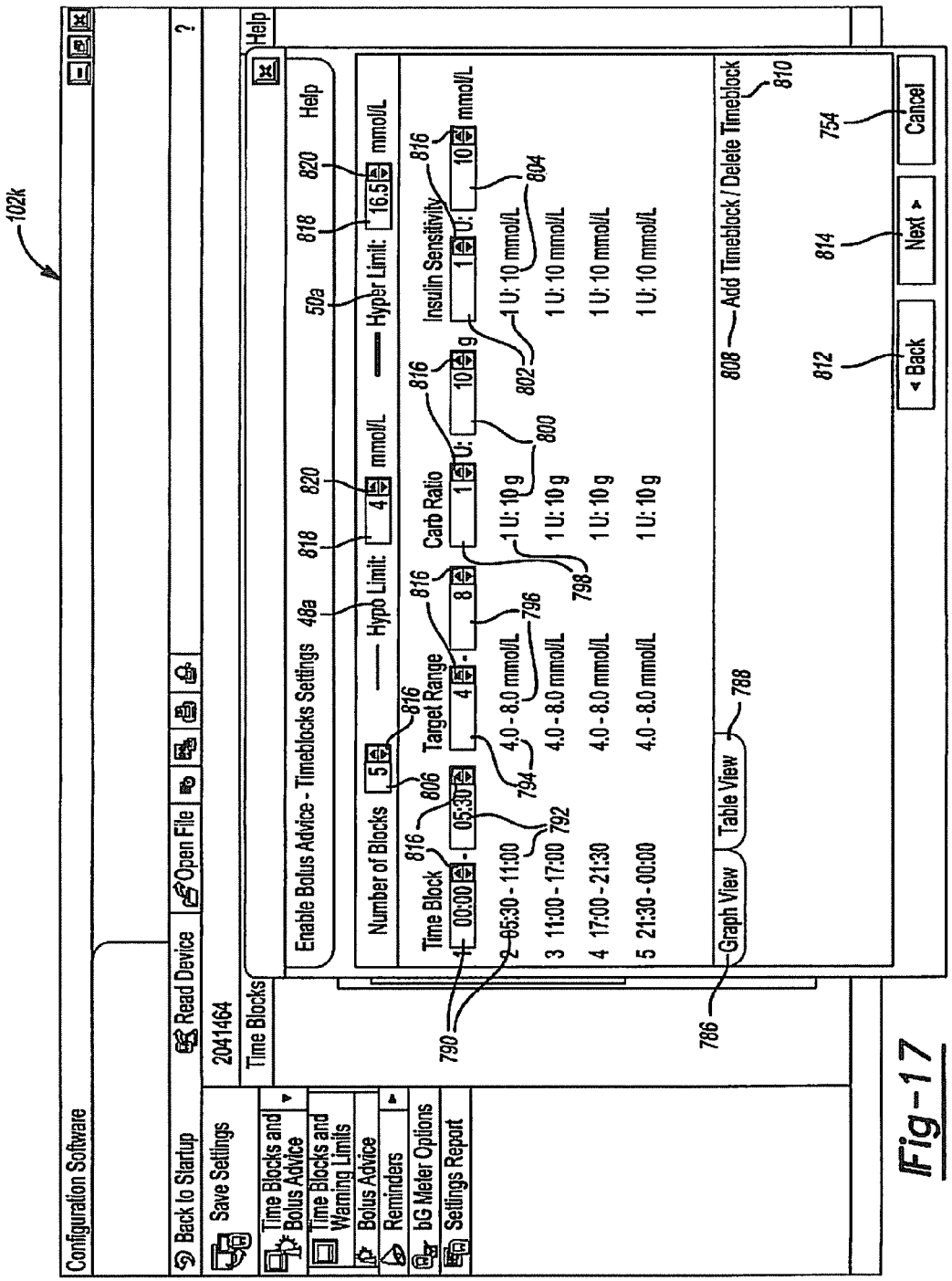
FIG. 17 illustrates an exemplary "Enable Bolus Advice-Table View" user interface.

At decision block 530, the method can determine if a "Table View" tab 788 has been selected (FIG. 16A). If the "Table View" tab 788 has been selected, then the method can go to block 534. Otherwise, the method can go to decision block 536. At block 534, the method can output the "Enable Bolus Advice-Table View" user interface 102k (FIG. 17). Then, the method can go to decision block 538. At decision block 538, the method can determine if user input has been received from the at least one user input device 16. If user input data 112 has been received, then the method can go to block 540. Otherwise, the method can loop until user input data 112 is received. At block 540, the method can save the user input data 112 as warning limit data 118, time block data 120 and bolus advice data 122. Then, the method can go to decision block 536.

At decision block 536, the method can determine if a "Graph View" tab 786 (FIG. 16A) has been selected. If the "Graph View" tab 786 was selected, then the method can go to C on FIG. 6. Otherwise, the method can go to decision block 542. At decision block 542, the method can determine if additional user input data 112 was received. If additional user input data 112 was received, the method can go to G on FIG. 8. Otherwise, the method can go to F on FIG. 7.

Figure 8:
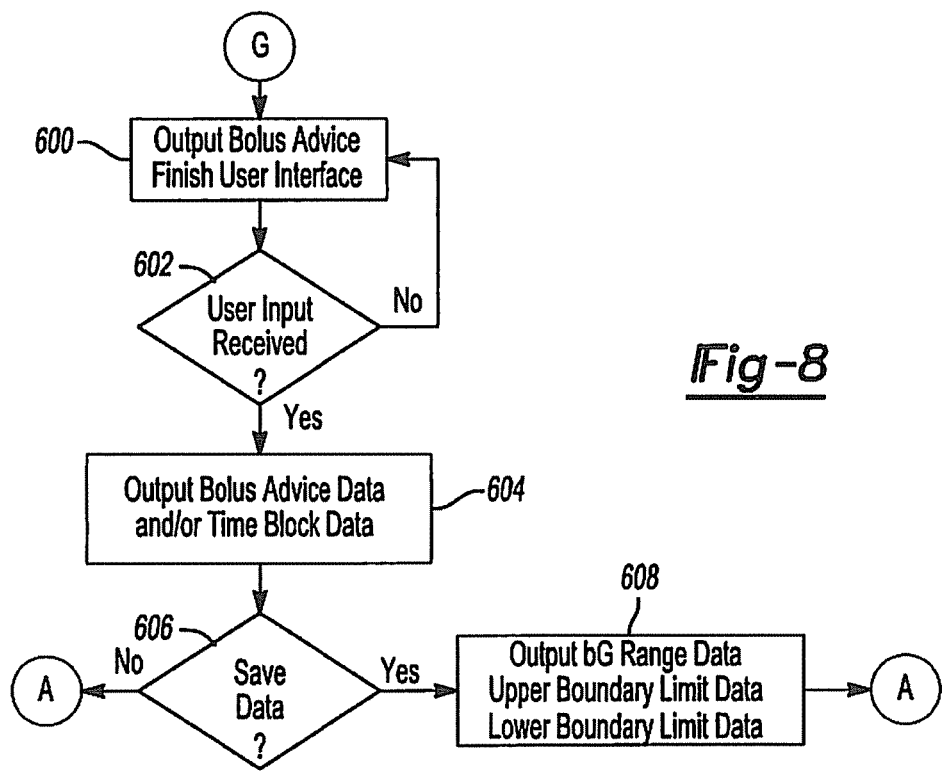
FIG. 8 is a continuation of the flowchart of FIG. 7 at G.
Figure 18:
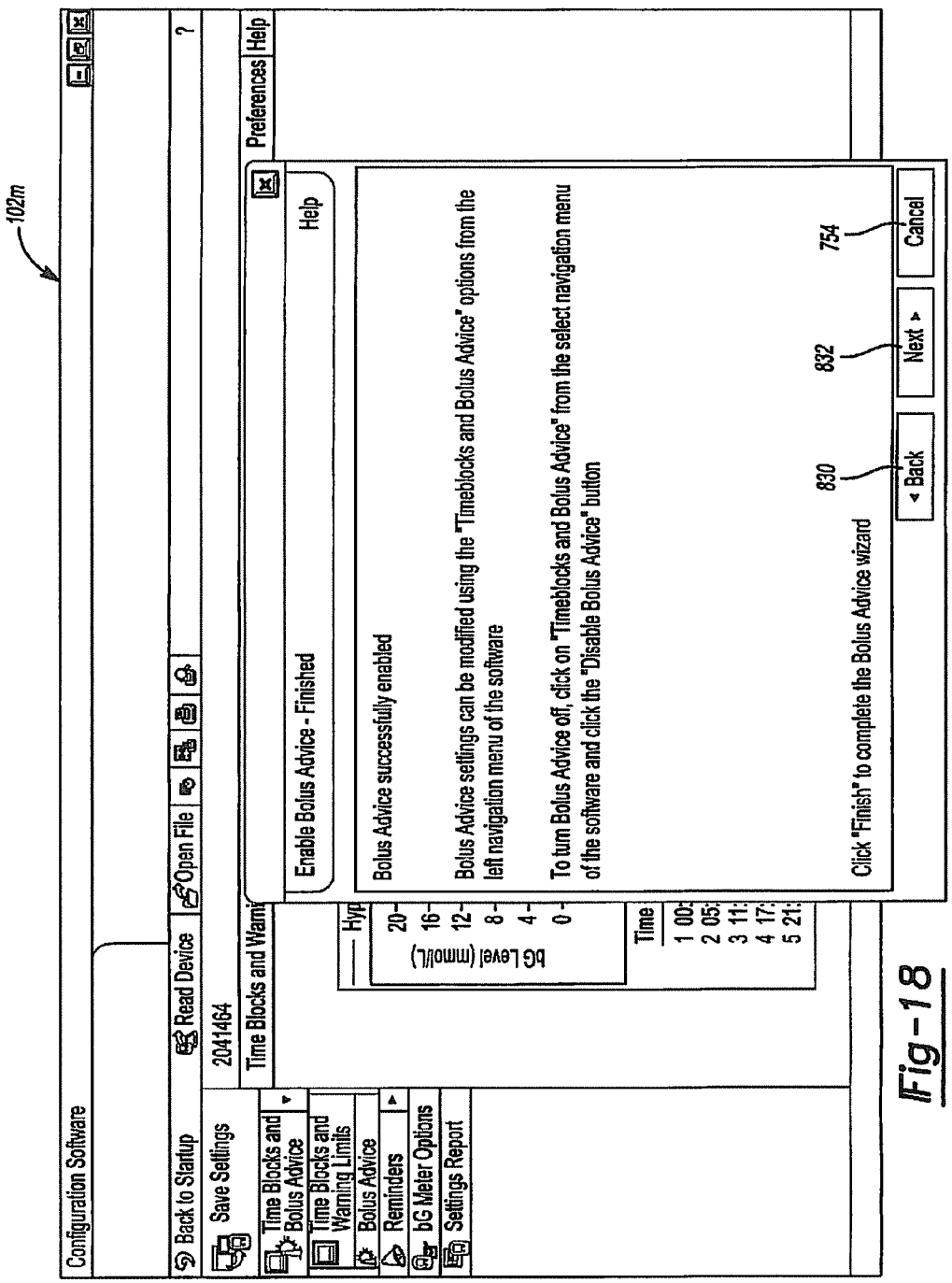
FIG. 18 illustrates an exemplary "Enable Bolus Advice-Finished" user interface.

With reference to FIG. 8, starting at G, the method can go to block 600. At block 600, the method can display the "Enable Bolus Advice-Finished" user interface 102m (FIG. 18). Then, the method can go to decision block 602. At decision block 602, the method can determine if user input data 112 has been received. If user input data 112 has been received, then the method can go to block 604. Otherwise, the method can loop to block 600. At block 604, the method can output bolus advice data 122 and/or time block data 120 on the user interface 102. At decision block 606, the method can determine if user input data 112 has been received to save the warning limit data 118, time block data 120 and bolus advice data 122. If a save data request has been received, then the method can output the warning limit data 118, time block data 120 and bolus advice data 122 saved in the data store 108 to the desired device, such as the hand-held diabetes device 24 or data storage device 28. Then, the method can go to A on FIG. 5. If a request to save data has not been received, then method can go to A on FIG. 5.

With reference to FIGS. 9-22, additional exemplary user interfaces 102 generated by the graphical user interface module 104 are illustrated. The user interface 102 can be formed of various user interfaces, such as, the "Time Blocks and Warning Limits" user interface 102a (FIG. 2), the "Startup" user interface 102b (FIG. 9), the "Read From Device-Prepare Device" user interface 102c (FIG. 10), a "Read From Device-Finished" user interface 102d (FIG. 11), the "Open a Settings File" user interface 102e (FIG. 12), the "Set Date and Time" user interface 102f (FIG. 13), the "Enable Bolus Advice-Start" user interface 102g (FIG. 14), the "Enable Bolus Advice-Health Events and Options" user interface 102h (FIG. 15), the "Enable Bolus Advice-Timeblocks Settings" user interface 102j (FIGS. 16A-16C), an "Enable Bolus Advice-Table View" user interface 102k (FIG. 17), an "Enable Bolus Advice-Finished" user interface 102m (FIG. 18), a "Save to a Device" user interface 102p (FIG. 19), a "Save to Device-Finished" user interface 102q (FIG. 20), the "Time Blocks" user interface 102r (FIG. 21) and the "Bolus Advice" user interface 102s (FIG. 22). The user interfaces 102g-102m (FIGS. 14-18) can generally comprise a bolus advice "wizard," which can guide the user through the act of inputting the warning limit data 118, time block data 120 and bolus advice data 122.

Figure 9:
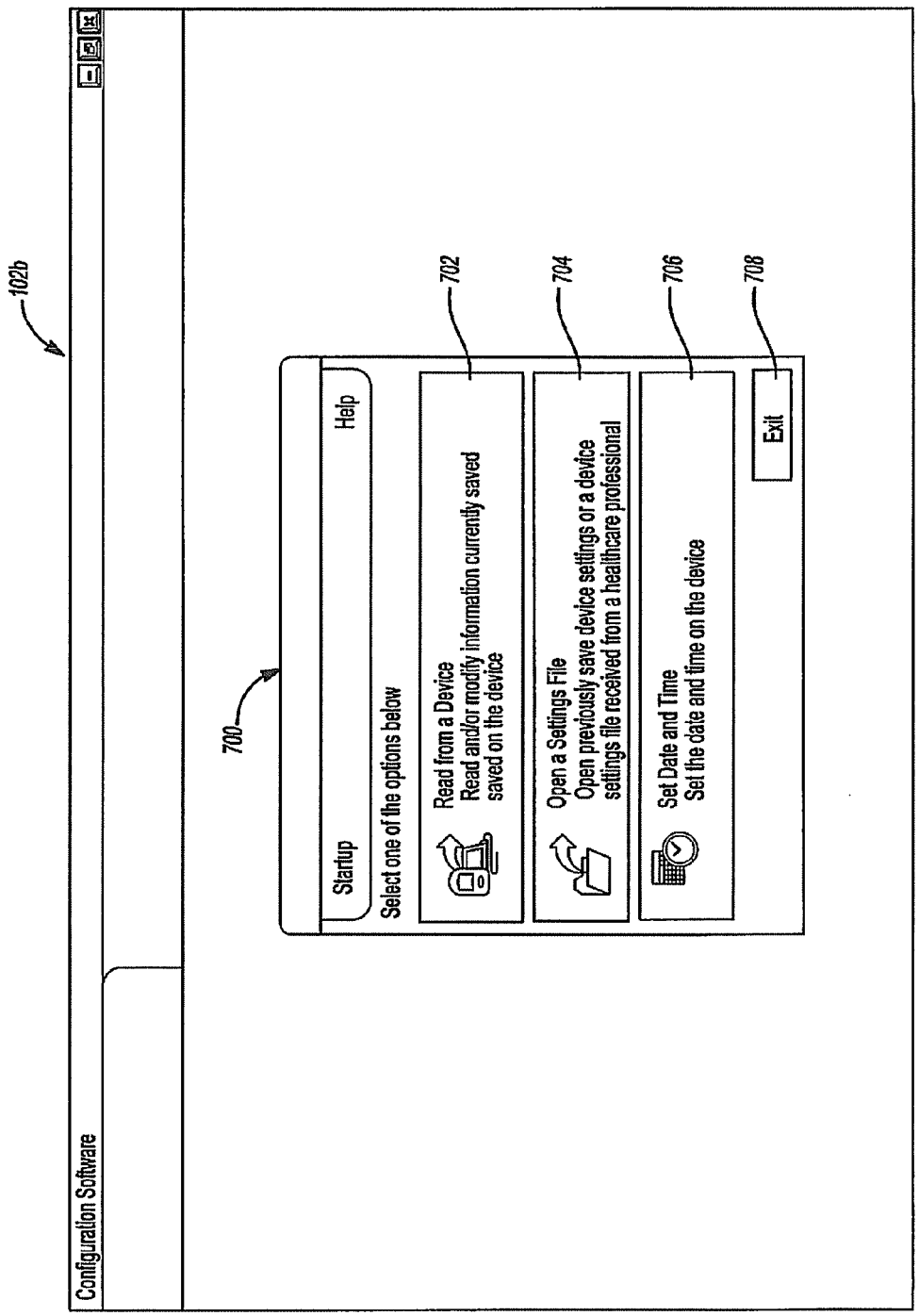
FIG. 9 illustrates an exemplary "Startup" user interface.

With reference to FIG. 9, the "Startup" user interface 102b can comprise an initial start-up screen for the computing system 10. The "Startup" user interface 102b can include a menu 700, which can include various options for the user to initialize the computing system 10. In one example, the menu 700 can include a "Read from Device" button 702, a "Open a Settings File" button 704 and a "Set Date and Time" button 706. The menu 700 can also include an "Exit" button 708, which can enable the user to exit the user interface 102.

Figure 10:
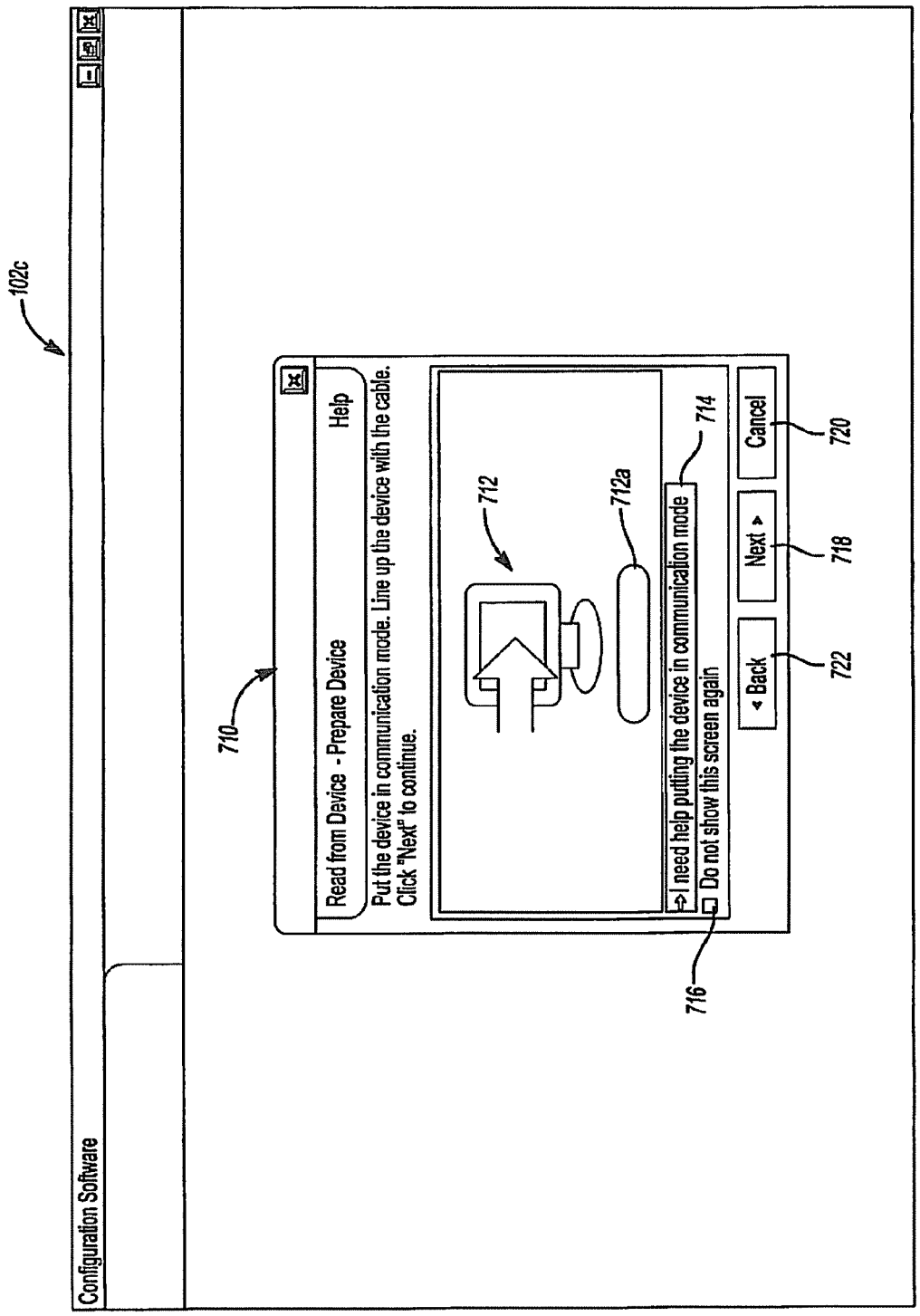
FIG. 10 illustrates an exemplary "Read From Device-Prepare Device" user interface.
Figure 12:
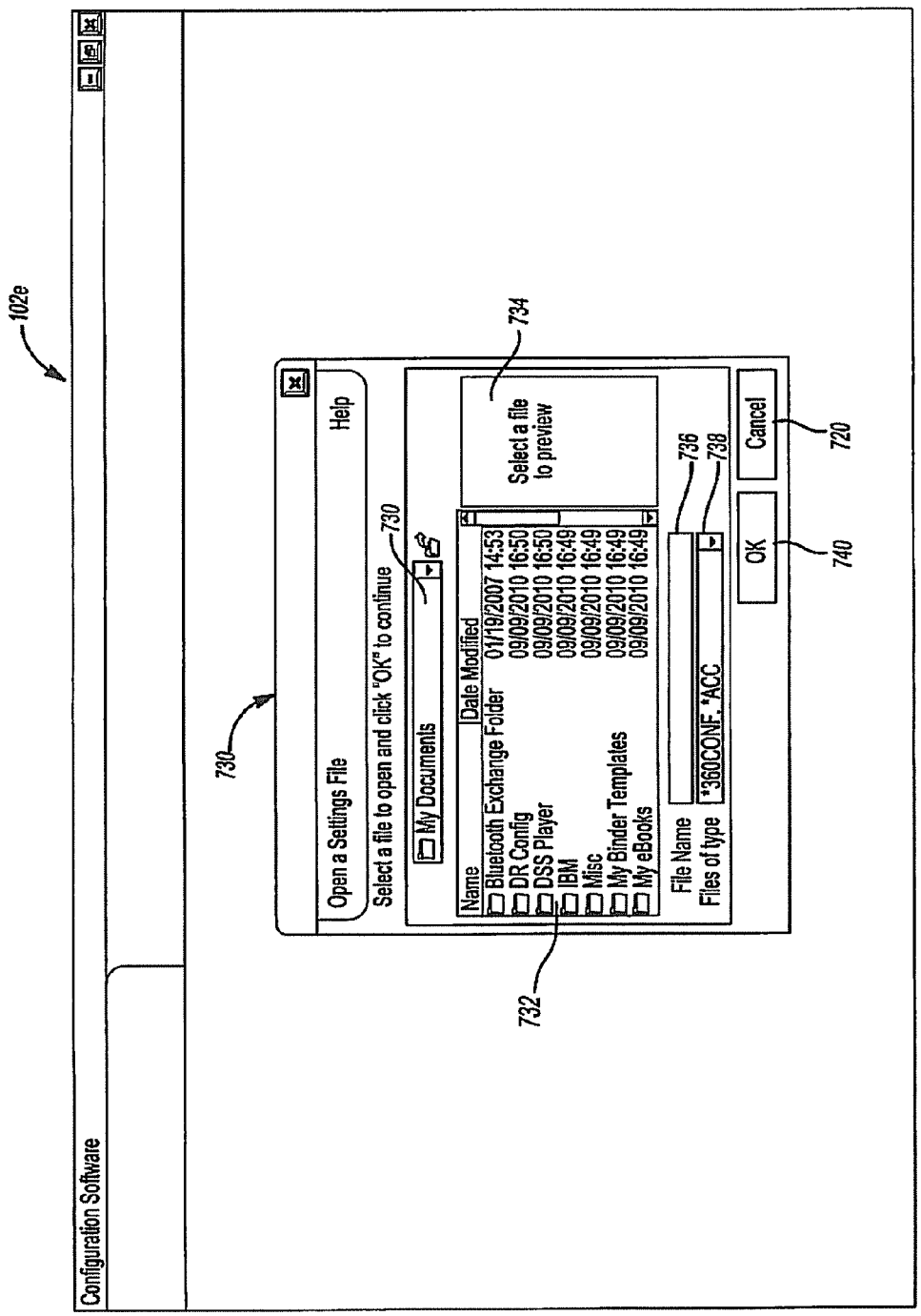
FIG. 12 illustrates an exemplary "Open a Settings File" user interface.

The "Read from Device" button 702, if selected, can begin a series of user interfaces 102 designed to retrieve the meter input data 128 from the hand-held diabetes device 24. In one example, the selection of the "Read from Device" button 702 can direct the user to the "Read From Device-Prepare Device" user interface 102c (FIG. 10). The "Open a Settings File" button 704 can allow the user to open a data file from the computing system 10 or the data storage device 28, for example. If the data is obtained from the data storage device 28, the data can comprise the data storage device input data 122. In one example, selecting the "Open a Settings File" button 704 can direct the user to the "Open a Settings File" user interface 102e (FIG. 12). The "Set Date and Time" button 706, if selected, can display the "Set Date and Time" user interface 102f (FIG. 13) to enable the user to set the date and time on the hand-held diabetes device 24.

Referring to FIG. 10, the "Read From Device-Prepare Device" user interface 102c can prompt the user to connect the hand-held diabetes device 24 to the computing system 10. In one example, the "Read From Device-Prepare Device" user interface 102c can include a display box 710, which can provide the user with textual instructions for placing the hand-held diabetes device 24 into communication with the computing system 10. The display box 710 can include a status indicator 712, a help link 714, a screen display selector 716, a "Next" button 718, a "Cancel" button 720 and a "Back" button 722.

The status indicator 712 can display a status of the connection between the hand-held diabetes device 24 and the computing system 10. For example, the status indicator 712 can include an indicator bar 712a, which can indicate the progress of the connection. The help link 714 can direct the user to a help screen user interface, which can further describe the process of placing the hand-held diabetes device 24 into communication with the computing system 10. The screen display selector 716 can enable the user to instruct the control module 100 to stop displaying the "Read From Device-Prepare Device" user interface 102c upon the selection of the "Read from Device" button 702. The "Next" button 718, if selected, can display the "Read From Device-Finished" user interface 102d. In other words, the selection of the "Next" button 718 can enable the user to continue in the process of obtaining the meter input data 118. The "Cancel" button 720 can enable the user to cancel reading from the hand-held diabetes device 14, and can redirect the user back to the "Startup" user interface 102b (FIG. 9). The "Back" button 722 can enable the user to go back to the "Startup" user interface 102b (FIG. 9).

Figure 11:
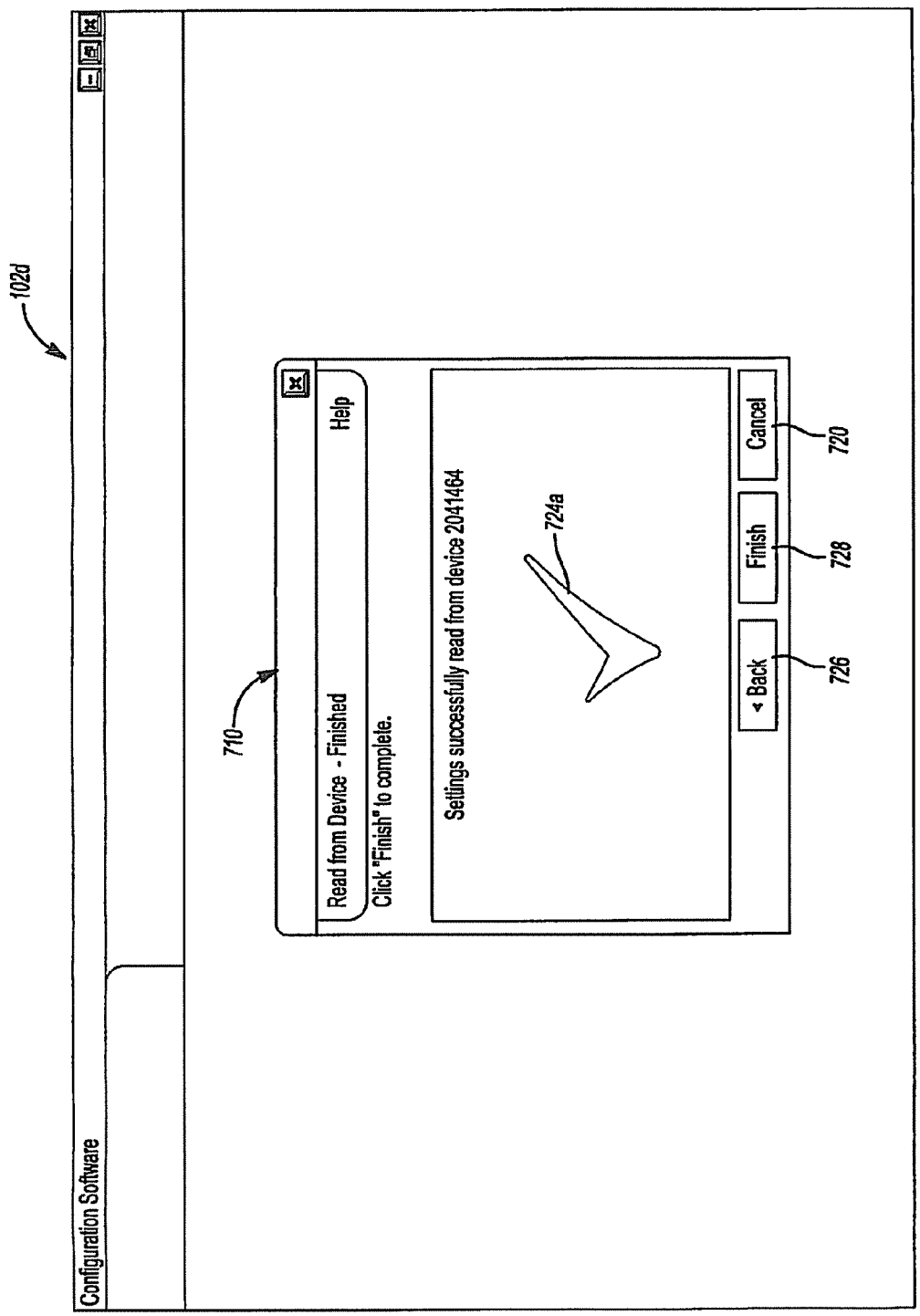
FIG. 11 illustrates an exemplary "Read From Device-Finished" user interface.

With regard to FIG. 11, the "Read From Device-Finished" user interface 102d can include a display box 724, which can graphically indicate to the user that the meter input data 118 has been successfully obtained from the hand-held diabetes device 24. In one example, the display box 724 can include an icon 724a, which can indicate that the meter input data 118 has been successfully received by the control module 100. The display box 724 can also include a "Back" button 726, a "Finish" button 728 and the "Cancel" button 720.

The "Back" button 726, if selected, can allow the user to go back to the "Read From Device-Prepare Device" user interface 102c. The "Finish" button 728 can allow the user to finish the process of obtaining the meter input data 118 from the hand-held diabetes device 24. The user can be prompted to select the "Finish" button 728 by instructions in the display box 724. If the "Finish" button 728 is selected, the control module 100 can display the "Time Blocks and Warning Limits" user interface 102a (FIG. 2).

With reference to FIG. 12, the "Open a Settings File" user interface 102e can allow the user to select a data file from the computing system 10 or the data storage device 28. The "Open a Settings File" user interface 102e can include a drop-down menu 730, a file information box 732, a file preview box 734, a "File Name" input box 736, a "Files of Type" drop-down menu 738, an "OK" button 740 and the "Cancel" button 720.

The drop-down menu 730 can provide a list of available sources on the computing system 10 for obtaining the data file, such as the data storage device 28. The file information box 732 can provide detailed information regarding the data files. The file preview box 734 can display an image of the data within the file. The "File Name" input box 736 can display the name of the data file, while the "Files of Type" drop-down menu 738 can enable the user to select the types of files to look for. The "OK" button 740, if selected, can prompt the control module 100 to load the data file as data storage input data 118.

Figure 13:
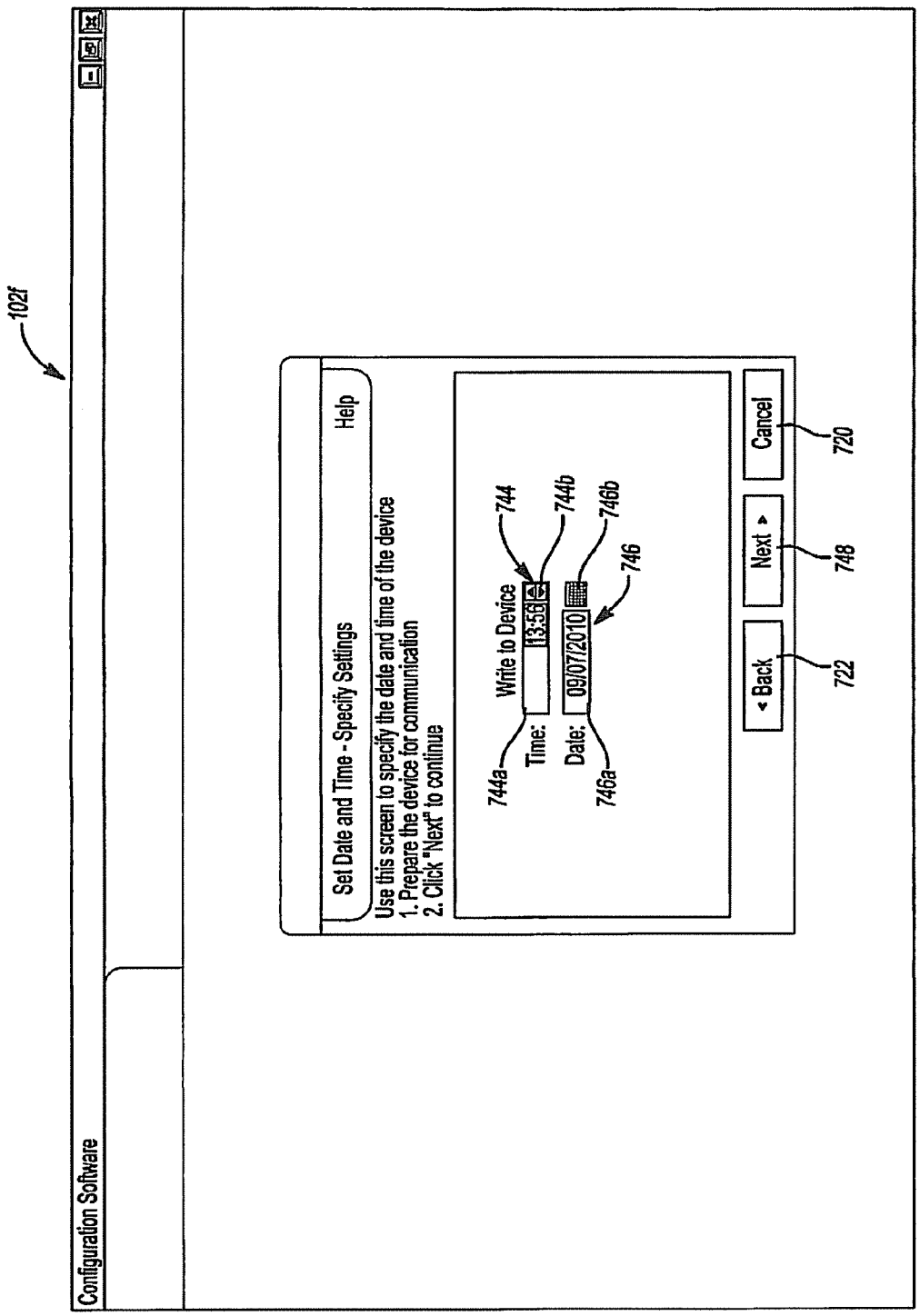
FIG. 13 illustrates an exemplary "Set Date and Time" user interface.

Referring to FIG. 13, the "Set Date and Time" user interface 102f can enable the user to set the date and time for the hand-held diabetes device 24. The "Set Date and Time" user interface 102f can include a time input box 744 and a date input box 746. The "Set Date and Time" user interface 102f can also include textual instructions to direct the user in placing the hand-held diabetes device 24 in communication with the computing system 10.

The time input box 744 can provide a text box 744a to enable a user to enter the text using the keyboard 16a, for example. The time input box 744 can also include one or more scroll selectors 744b, which can enable the user to use the pointing device 16b to incrementally adjust the time. The date input box 746 can include a text box 746a to enable a user to enter the text using the keyboard 16a, for example. The date input box 746 can also include a calendar button 746b, which can prompt a calendar user interface to enable the user to select a specific date from a given month or months.

The "Set Date and Time" user interface 102f can also include the "Back" button 722, a "Next" button 748 and the "Cancel" button 720. The "Next" button 748, if selected, can cause the control module 100 to save the date and time to the hand-held diabetes device 24. The selection of the "Next" button 748 can also prompt the control module 100 to display a user interface that indicates that the hand-held device 24 has been updated or the control module 100 could display the "Startup" user interface 102b.

In FIG. 14, the "Enable Bolus Advice-Start" user interface 102g can provide the user with textual information with regard to using the control module 100 to set the warning limit data 118, time block data 120 and bolus advice data 122. The "Enable Bolus Advice-Start" user interface 102g can include a "Back" button 750, a "Next" button 752 and a "Cancel" button 754. The "Back" button 750, if selected, can display the "Time Blocks and Warning Limits" user interface 102a (FIG. 2). The "Next" button 752, if selected, can display the "Enable Bolus Advice-Health Events and Options" user interface 102h (FIG. 15). The "Cancel" button 754, if selected, can display the "Time Blocks and Warning Limits" user interface 102a (FIG. 2).

With regard to FIG. 15, the "Enable Bolus Advice-Health Events and Options" user interface 102h can allow the user to input their specific health events and desired options with regard to bolus insulin advice. In one example, the "Enable Bolus Advice-Health Events and Options" user interface 102h can include a "Health Events" input menu 760 and an "Options" input menu 762.

The "Health Events" input menu 760 can include a first "Exercise" input box 764, a second "Exercise" box 765, a "Stress" input box 766, an "Illness" input box 768 and a "Premenstrual" input box 770. The user can input values that specify a percentage that each of these events may impact their bG level. Each of the input boxes 764, 765, 766, 768, 770 can include a scroll selector 772, which can enable the user to use the pointing device 16b to incrementally adjust the percentages for each of the first "Exercise" input box 764, second "Exercise" box 765, "Stress" input box 766, "Illness" input box 768 and "Premenstrual" input box 770.

The "Options" input menu 762 can include various options that the user can use to adjust the bolus advice data 122. In one example, the "Options" input menu 762 can include a "Meal Rise" input box 772, a "Snack Size" input box 774, an "Acting Time" input box 776 and an "Offset Time" input box 778. Each of the input boxes 772, 774, 776, 778 can include a scroll selector 780, which can enable the user to use the pointing device 16b to incrementally adjust the percentages for each of the "Meal Rise" input box 772, "Snack Size" input box 774, "Acting Time" input box 776 and "Offset Time" input box 778.

The "Enable Bolus Advice-Health Events and Options" user interface 102h can also include a "Back" button 782, a "Next" button 784 and the "Cancel" button 754. The "Back" button 782, if selected, can display the "Enable Bolus Advice-Start" user interface 102g (FIG. 14). The "Next" button 784, if selected, can display the "Enable Bolus Advice-Timeblocks Settings" user interface 102j (FIGS. 16A-16C).

With reference to FIGS. 16A-16C, the "Enable Bolus Advice-Timeblocks Settings" user interface 102j (FIGS. 16A-16C) is illustrated. The "Enable Bolus Advice-Timeblocks Settings" user interface 102j can include the bar chart 32 including the plurality of bar structures 30, the x-axis 44, the y-axis 46, the lower boundary line 48 and upper boundary line 50. In this example, the second bar structure 30b can be selected, and can be graphically illustrated in a different color, for example, to indicate to the user that the second bar structure 30b has been selected.

The "Enable Bolus Advice-Timeblocks Settings" user interface 102j can also include a "Graph View" tab 786, a "Table View" tab 788, a "Time Block" start input box 790, a "Time Block" end input box 792, a "Target Range" start input box 794, a "Target Range" end input box 796, a "Carb Ratio" unit input box 798, a "Carb Ratio" gram input box 800, an "Insulin Sensitivity" unit box 802 and an "Insulin Sensitivity" adjustment level input box 804. The "Enable Bolus Advice-Timeblocks Settings" user interface 102j can also include a "Number of Blocks" input box 806, an "Add Time Block" link 808, a "Delete Time Block" link 810, a "Back" button 812, a "Next" button 814 and the "Cancel" button 754.

The "Graph View" tab 786 can cause the display of the bar chart 32, as illustrated in FIG. 16A. The "Table View" tab 788 can cause the display of the "Enable Bolus Advice-Table View" user interface 102k (FIG. 17). Each of the input boxes 790, 792, 796, 798, 800, 802, 804, 806 can include a scroll selector 816, which can enable the user to use the pointing device 16b to incrementally adjust the data values for each of the "Time Block" start input box 790, Time Block" end input box 792, "Target Range" start input box 794, "Target Range" end input box 796, "Carb Ratio" unit input box 798, "Carb Ratio" gram input box 800, "Insulin Sensitivity" unit input box 802, "Insulin Sensitivity" adjustment level input box 804 and "Number of Blocks" input box 806.

The "Time Block" start input box 790 can allow the user to manually enter the start time for the selected bar structure 30b through the keyboard 16a. The "Time Block" end input box 792 can allow the user to manually enter the end time for the selected bar structure 30b through the keyboard 16a. The "Target Range" start input box 794 can allow the user to manually enter the starting bG level for the range of bG level associated with the selected bar structure 30b through the keyboard 16a. The "Target Range" end input box 796 can allow the user to manually enter the ending bG level for the range of bG level associated with the selected bar structure 30b through the keyboard 16a. The data entered into the "Time Block" start input box 790, "Time Block" end input box 792, "Target Range" start input box 794 and "Target Range" end input box 796 can be saved as time block data 120.

It should be noted that although the "Enable Bolus Advice-Timeblocks Settings" user interface 102j includes the Time Block" start input box 790, "Time Block" end input box 792, "Target Range" start input box 794 and "Target Range" end input box 796, the user need not input data into these input boxes 790, 792, 794, 796 in order to modify or manipulate the time block data 120. Rather, the user can use the pointing device 16b, for example, to adjust one or more of the left side 36, right side 38, top side 40 and bottom side 42 of the selected bar structure 30. For example, with reference to FIG. 16B, the pointing device 16b can be used to adjust the top side 40 of the sixth bar structure 30f.

Additionally, while the "Hypo Limit" 48a and "Hyper Limit" 50a are illustrated herein as including a text input box 818 for allowing the user to input the hypoglycemic and hyperglycemic warning limits, the "Hypo Limit" 48a and the "Hyper Limit" 50a can also include a scroll selector 820 to enable the user to use the pointing device 16b to incrementally adjust the locations of the upper boundary line 50 and lower boundary line 48. Furthermore, with reference to FIG. 16C, the pointing device 16b could be used to manipulate or move the location of the lower boundary line 48 and upper boundary line 50 to the desired hypoglycemic warning limit and hyperglycemic warning limit. The locations of the lower boundary line 48 and the upper boundary line 50 can be saved as warning limit data 118.

The "Carb Ratio" unit input box 798 can allow the user to adjust the units of insulin required for a particular number of carbohydrates. The "Carb Ratio" gram input box 800 can cooperate with the "Carb Ratio" unit input box 798 to enable the user to set the number of carbohydrates that correspond to a particular unit of insulin. The "Carb Ratio" unit input box 798 and the "Carb Ratio" gram input box 800 can be saved as a portion of the bolus advice data 122.

The "Insulin Sensitivity" unit input box 802 can allow the user to select a number of units of insulin required to adjust their bG level a particular increment. The "Insulin Sensitivity" adjustment level input box 804 can cooperate with the "Insulin Sensitivity" unit input box 802 to enable the user to set the particular increment of bG level change for the number of units of insulin. The "Insulin Sensitivity" unit input box 802 and the "Insulin Sensitivity" adjustment level input box 804 can be saved as a portion of the bolus advice data 122.

The "Number of Blocks" input box 806 can enable the user to input a desired number of bar structures 30 for display on the bar chart 32, subject to the constraint data 130. The "Add Time Block" link 808, if selected, can cause the display of an additional bar structure 30, which in one example can be added adjacent to the fifth bar structure 30e. For example, with reference to FIG. 16B, a sixth bar structure 30f can be inserted adjacent to the fifth bar structure 30e. It should be noted that the example of FIG. 16B is merely exemplary, as the "Add Time Block" link 808 could cause the insertion of a bar structure 30 adjacent to the selected bar structure 30, or could display a user interface to enable the user to select the location on the bar chart 32 for the new bar structure 30. The "Delete Time Block" link 810, if selected, can cause the removal of the selected bar structure 30 from the bar chart 32.

The "Back" button 812, if selected, can cause the display of the "Enable Bolus Advice-Health Events and Options" user interface 102*h* (FIG. 15). The "Next" button 814, if selected, can cause the display of the "Enable Bolus Advice-Finished" user interface 102*m* (FIG. 18).

With reference to FIG. 17, the "Enable Bolus Advice-Table View" user interface 102*k* is illustrated. The "Enable Bolus Advice-Table View" user interface 102*k* can provide an alternative user interface for the population of the warning limit data 118, time block data 120 and bolus advice data 122. In other words, the "Enable Bolus Advice-Table View" user interface 102*k* can provide a tabular or chart-like representation of the data displayed on the "Enable Bolus Advice-Timeblocks Settings" user interface 102*j*. Thus, the "Enable Bolus Advice-Table View" user interface 102*k* can include the text input box 818 and scroll selector 820 for the "Hypo Limit" 48*a* and "Hyper Limit" 50*a*, the "Graph View" tab 786, the "Table View" tab 788, a plurality of "Time Block" start input boxes 790, a plurality of "Time Block" end input boxes 792, a plurality of "Target Range" start input boxes 794, a plurality of "Target Range" end input boxes 796, a plurality of "Carb Ratio" unit input boxes 798, a plurality of "Carb Ratio" gram input boxes 800, a plurality of "Insulin Sensitivity" unit boxes 802 and a plurality of "Insulin Sensitivity" adjustment level input boxes 804. The "Enable Bolus Advice-Table View" user interface 102*k* can also include the "Number of Blocks" input box 806, the "Add Time Block" link 808, the "Delete Time Block" link 810, the "Back" button 812, the "Next" button 814 and the "Cancel" button 754.

With regard to FIG. 18, the "Enable Bolus Advice-Finished" user interface 102*m* can provide the user with textual information with regard to performing additional modifications to the warning limit data 118, time block data 120 and bolus advice data 122. The "Enable Bolus Advice-Finished" user interface 102*m* can also provide the user with textual information with regard to disabling the bolus advice data 122. The "Enable Bolus Advice-Finished" user interface 102*m* can include a "Back" button 830, a "Finish" button 832 and the "Cancel" button 754. The "Back" button 830, if selected, can display the "Enable Bolus Advice-Timeblocks Settings" user interface 102*j*. The "Finish" button 832, if selected, can display the "Time Blocks and Warning Limits" user interface 102*a* (FIG. 2). The "Cancel" button 754, if selected, can display the "Time Blocks and Warning Limits" user interface 102*a* (FIG. 2).

Figure 19:
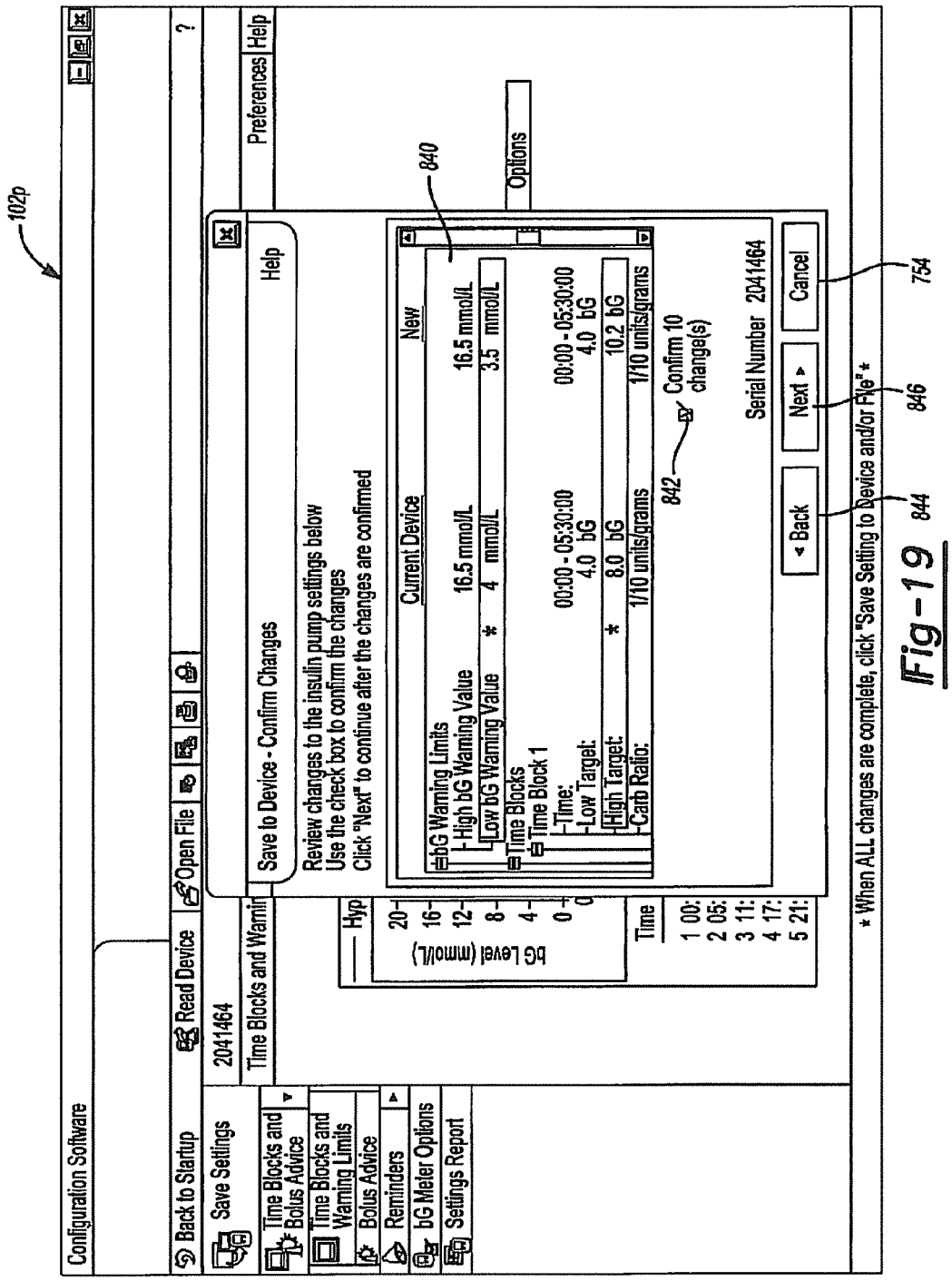
FIG. 19 illustrates an exemplary "Save to a Device" user interface.

Referring to FIG. 19, the "Save to a Device" user interface 102*p* can be displayed upon selection of the "Save Settings" selector 62. The "Save to a Device" user interface 102*p* can allow the user to confirm the changes to the warning limit data 118, time block data 120 and bolus advice data 122 prior to saving these data values to the hand-held diabetes device 24. In one example, the "Save to a Device" user interface 102*p* can include a summary chart 840, which can display in a list form the warning limit data 118, time block data 120 and bolus advice data 122 currently on the hand-held diabetes device 24 and the warning limit data 118, time block data 120 and bolus advice data 122 that has been input into the user interfaces 102 via the at least one user input device 16. The "Save to a Device" user interface 102*p* can also include a "Confirm Changes" selector 842, a "Back" button 844, a "Next" button 846 and the "Cancel" button 754. The "Back" button 844, if selected, can display the "Time Blocks and Warning Limits" user interface 102*a* (FIG. 2). The "Next" button 846, if selected, can display the "Save to Device-Finished" user interface 102*q* (FIG. 20).

Figure 20:
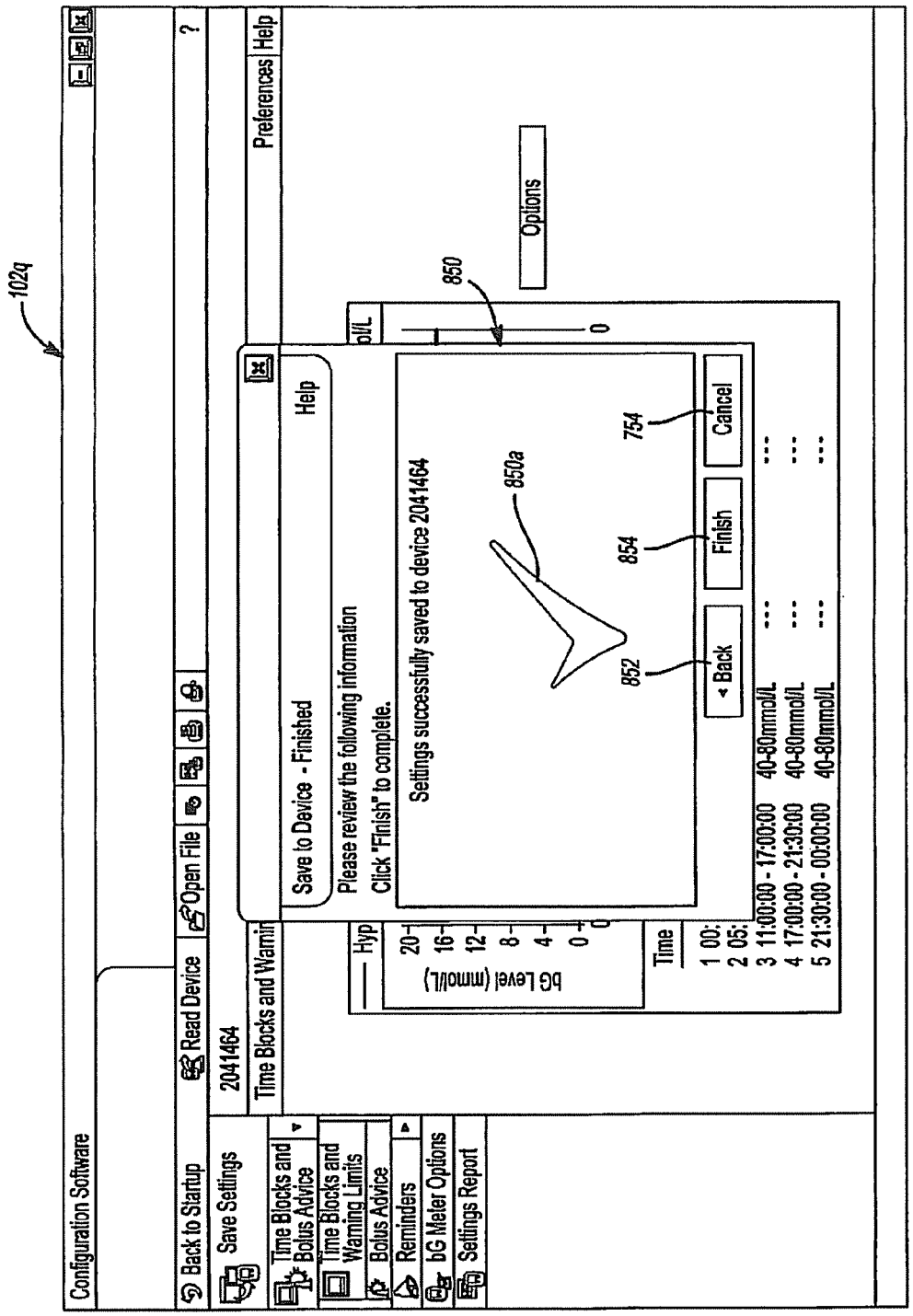
FIG. 20 illustrates an exemplary "Save to Device-Finished" user interface.

With regard to FIG. 20, the "Save to Device-Finished" user interface 102*q* can include a display box 850, which can graphically indicate to the user that the meter data 124 has been successfully saved to the hand-held diabetes device 24. In one example, the display box 850 can include an icon 850*a*, which can indicate that the meter data 124 has been successfully output. The display box 850 can also include a "Back" button 852, a "Finish" button 854 and a "Cancel" button 754. The "Back" button 852, if selected, can display the "Save to a Device" user interface 102*p* (FIG. 19). The "Finish" button 854, if selected, can display the "Time Blocks and Warning Limits" user interface 102*a* (FIG. 2).

Figure 21:
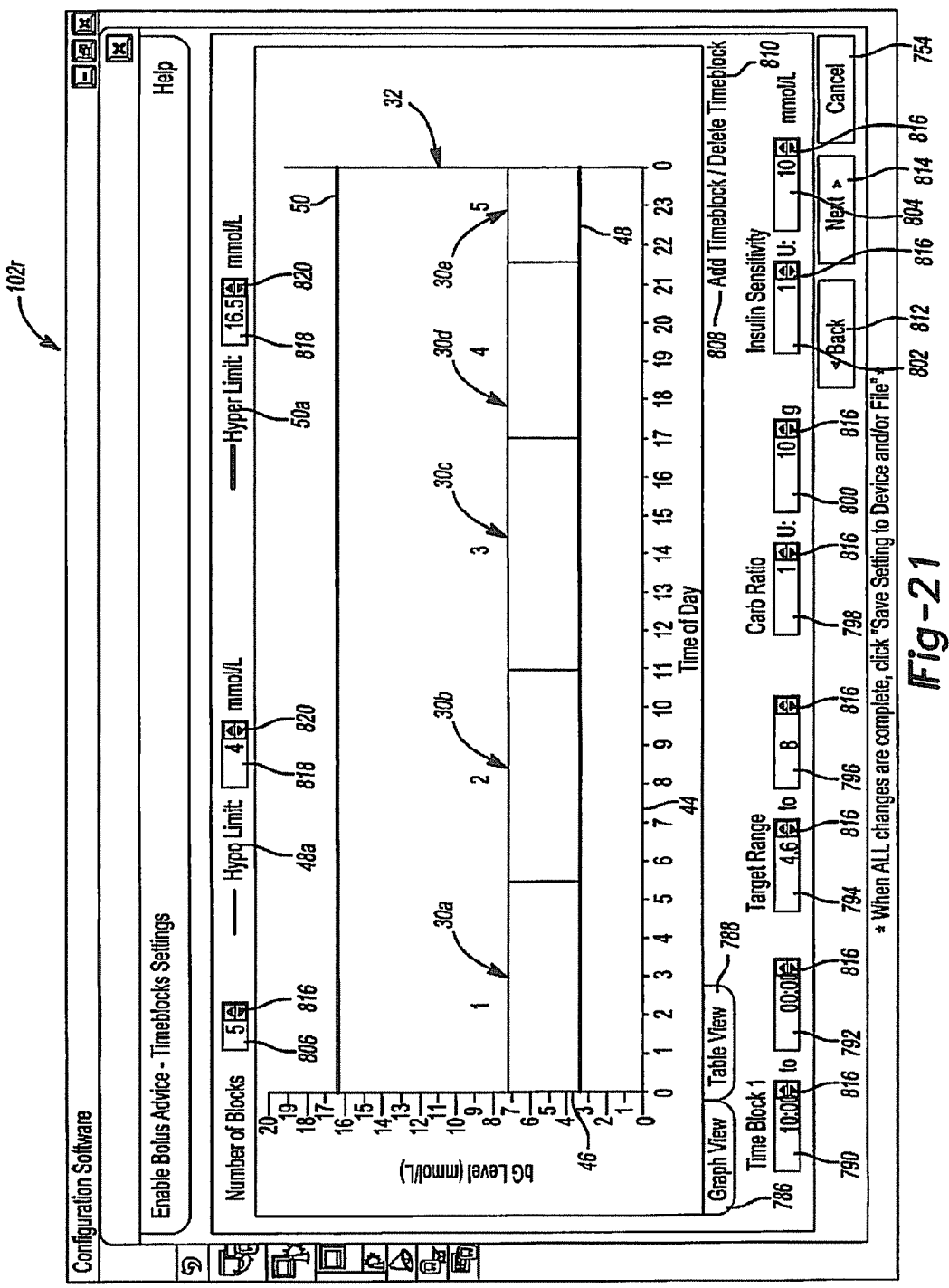
FIG. 21 illustrates an exemplary "Time Blocks" user interface.

In FIG. 21, the "Time Blocks" user interface 102*r* can graphically illustrate substantially the same data as the "Enable Bolus Advice-Timeblocks Settings" user interface 102*j*, and thus, the "Time Blocks" user interface 102*r* will not be discussed in great detail herein. Briefly, however, the "Time Blocks" user interface 102*r* can also include an "OK" button 860 and the "Cancel" button 754. The "OK" button 860, if selected, can display the "Time Blocks and Warning Limits" user interface 102*a* (FIG. 2).

With reference to FIG. 22, the "Bolus Advice" user interface 102*s* is illustrated. The "Bolus Advice" user interface 102*s* can be substantially similar to the "Enable Bolus Advice-Health Events and Options" user interface 102*h* (FIG. 15), and thus, the "Bolus Advice" user interface 102*s* will not be discussed in great detail herein. Briefly, however, the "Bolus Advice" user interface 102*s* can include the "Bolus Advice" button 54, which can enable or disable the bolus advice data 122.

Thus, the user interfaces 102 generated by the control module 100 can provide the user with an efficient and easy manner to modify or view the warning limit data 118, time-block data 120 and bolus advice data 122 and save those modifications to the hand-held diabetes device 24. In other words, the computing system 10 can enable modification of insulin therapy support parameters such as a start time of day data value, an end time of day data value, a lower blood glucose target data value, an upper blood glucose target data value, a high blood glucose warning data value and a low blood glucose warning data value on a hand-held diabetes management device. The system can include a graphical user interface module that creates a graphical user interface having a plurality of bar structures positionable on or between a first line that graphically illustrates an upper boundary limit and a second line that graphically indicates a lower boundary limit.

Each of the plurality of bar structures can have a first side that graphically indicates a start time of a time window opposite a second side that graphically indicates an end time of the time window and a third side that graphically indicates a start value for a range of values opposite a fourth side that graphically indicates an end value for the range of values. The first side, the second side, the third side and the fourth side of each of the plurality of bar structures, the first line and the second line can be adjustable by a user input. The plurality of bar structures can be governed by a set of constraints that confine each of the plurality of bar structures to an area defined by the first line and the second line and to a unique time window.

The system can also include a data store for storing at least the start time of day data value, the end time of day data value, the lower blood glucose target data value, the upper blood glucose target data value, the high blood glucose warning data value and the low blood glucose warning data value. The system can further include a data mapping module that maps for each of the plurality of bar structures on the graphical user interface the start time of day data value to a location of the first side, the end time of day data value to a location of the second side, the lower blood glucose target data value to a location of the third side and the upper blood glucose target data value to a location of the fourth side and stores the start time of day data value, end time of day data value, lower blood glucose target data value and upper blood glucose target data value in the data store. The data mapping module can also map the high blood glucose warning data value to a location of the first line and map the low blood glucose warning data value to a location of the second line. The data mapping module can store the high blood glucose warning data value and the low blood glucose warning data value in the data store.

In addition, the set of constraints can confine the second line to an area below the first line. The system can also include that the graphical user interface comprises a graphical illustration of a bar chart, which includes a time of day in hours on an x-axis and a blood glucose measurement on a y-axis. The plurality of bar structures can be graphically illustrated on the bar chart. Further, the third side of at least one of the plurality of bar structures is located above the x-axis so as to not be in contact with the x-axis. The graphical user interface can also comprise at least one input box for receipt of data relating to a carb ratio, insulin sensitivity and combinations thereof.

The system can further comprise the hand-held diabetes management device, and the data mapping module can output the start time of day data value, the end time of day data value, the lower blood glucose target data value, the upper blood glucose target data value, the high blood glucose warning data value and the low blood glucose warning data value to the hand-held diabetes management device.

Additionally, the graphical user interface module, data store and data mapping module of the system can be implemented on a computer readable medium on a computing device, and the hand-held diabetes management device can be in communication with the computing device through a wireless connection, a wired connection or combinations thereof.

The system can also include a user input device selected from the group comprising: touchpad, touch pen, touch screen, keyboard, mouse, joystick, trackball, wireless mouse, pointing device and combinations thereof.

Further provided is a system for modifying insulin therapy support parameters such as a start time of day data value, an end time of day data value, a lower blood glucose target data value, an upper blood glucose target data value, a high blood glucose warning data value and a low blood glucose warning data value on a hand-held diabetes management device. The system can include a graphical user interface module that creates a graphical user interface illustrating a bar chart having a plurality of bar structures, an x-axis graphically illustrating a time of day and a y-axis graphically illustrating a blood glucose level. The plurality of bar structures can be positionable on the bar chart, and each of the plurality of bar structures can have a first side that graphically indicates a start time of day opposite a second side that graphically indicates an end time of day and a third side that graphically indicates a lower target value for a blood glucose level opposite a fourth side that graphically indicates an upper target value for the blood glucose level. The first side, the second side, the third side and the fourth side of each of the plurality of bar structures can be adjustable by a user input. The third side of at least one of the plurality of bar structures can be spaced apart from the x-axis.

The system can also include a data store for storing at least the start time of day data value, the end time of day data value, the lower blood glucose target data value and the upper blood glucose target data value. The system can include a data mapping module that maps for each of the plurality of bar structures on the graphical user interface the start time of day data value to a location of the first side, the end time of day data value to a location of the second side, the lower blood glucose target data value to a location of the third side and the upper blood glucose target data value to a location of the fourth side and stores the start time of day data value, end time of day data value, lower blood glucose target data value and upper blood glucose target data value in the data store. The data mapping module can output the start time of day data value, end time of day data value, lower blood glucose target data value and upper blood glucose target data value to the hand-held diabetes management device.

In addition, the graphical user interface can further comprise a first line that graphically illustrates an upper boundary limit and a second line that graphically illustrates a lower boundary limit, the first line and second line each being graphically illustrated on the bar chart as horizontal lines. The first line and the second line can be adjustable by a user input. The second line can be positioned on the bar chart above the x-axis, such that the second line graphically represents a blood glucose level value greater than zero. The graphical user interface can further comprise at least one input box for receipt of data relating to a carb ratio, insulin sensitivity and combinations thereof.

Additionally, the data store further can store a high blood glucose warning data value and a low blood glucose warning data value, and the data mapping module can map the high blood glucose warning data value to a location of the first line and can map the low blood glucose warning data value to a location of the second line.

Furthermore, the plurality of bar structures can be governed by a set of constraints that confine each of the plurality of bar structures to an area defined by the first line and the second line. The first side and the second side of each of the plurality of bar structures cooperate to form a time window, and the set of constraints further confines the time window defined by the first side and the second side of each of the plurality of bar structures to a unique time window. The number of the plurality of bar structures displayed on the graphical user interface can be adjustable by user input.

The system can also include the graphical user interface module, data store and data mapping module being implemented on a computer readable medium on a computing device, and the hand-held diabetes management device being in communication with the computing device through a wireless connection, a wired connection or combinations thereof.

While specific examples have been described in the specification and illustrated in the drawings, it will be understood by those of ordinary skill in the art that various changes may be made and equivalents may be substituted for elements thereof without departing from the scope of the present disclosure as defined in the claims. Furthermore, the mixing and matching of features, elements and/or functions between various examples is expressly contemplated herein so that one of ordinary skill in the art would appreciate from this disclosure that features, elements and/or functions of one example may be incorporated into another example as appropriate, unless described otherwise, above. Therefore, it is intended that the present disclosure not be limited to the particular examples illustrated by the drawings and described in the specification as the best mode presently contemplated for carrying out this disclosure, but that the scope of the present disclosure will include any embodiments falling within the foregoing description and the appended claims.

What is claimed is:

1. A diabetes manager for modifying insulin therapy support parameters including a start time of day data value, an end time of day data value, a lower blood glucose target data value, an upper blood glucose target data value, a high blood glucose warning data value and a low blood glucose warning data value on a hand-held diabetes management device comprising:

a graphical user interface module, a data store, and a data mapping module implemented on a non-transitory computer readable medium on a computing device, wherein the computing device communicates with a hand-held diabetes management device;

the graphical user interface module being configured to create a graphical user interface having a plurality of bar structures positionable on or between a first line that graphically indicates an upper boundary limit and a second line that graphically indicates a lower boundary limit, each of the plurality of bar structures having a first side that graphically indicates a start time of a time window opposite a second side that graphically indicates an end time of the time window and a third side that graphically indicates a start value for a range of values opposite a fourth side that graphically indicates an end value for the range of values;

the first side, the second side, the third side and the fourth side of each of the plurality of bar structures, the first line and the second line adjustable by a user input;

the plurality of bar structures governed by a set of constraints that confine each of the plurality of bar structures to an area defined by the first line and the second line and to a unique time window;

the data store being configured to store at least a start time of day data value, an end time of day data value, a lower blood glucose target data value, an upper blood glucose target data value, a high blood glucose warning data value and a low blood glucose warning data value;

the data mapping module being configured to map for each of the plurality of bar structures on the graphical user interface the start time of day data value to a location of the first side, the end time of day data value to a location of the second side, the lower blood glucose target data value to a location of the third side and the upper blood glucose target data value to a location of the fourth side and stores the start time of day data value, the end time of day data value, the lower blood glucose target data value and the upper blood glucose target data value in the data store; and wherein the data mapping module maps the high blood glucose warning data value to a location of the first line and maps the low blood glucose warning data value to a location of the second line and stores the high blood glucose warning data value and the low blood glucose warning data value in the data store.

2. A diabetes manager of claim 1, wherein the set of constraints confines the second line to an area below the first line.

3. A diabetes manager of claim 1, wherein the graphical user interface is configured to create a graphical illustration of a bar chart, which includes a time of day in hours on an x-axis and a blood glucose measurement on a y-axis.

4. A diabetes manager of claim 3, wherein the plurality of bar structures are graphically illustrated on the bar chart.

5. A diabetes manager of claim 4, wherein the third side of at least one of the plurality of bar structures is located above the x-axis so as to not be in contact with the x-axis.

6. A diabetes manager of claim 1, wherein the data mapping module outputs the start time of day data value, the end time of day data value, the lower blood glucose target data value, the upper blood glucose target data value, the high blood glucose warning data value and the low blood glucose warning data value to the hand-held diabetes management device.

7. A diabetes manager of claim 1, wherein the hand-held diabetes management device is in communication with the computing device through a wireless connection, a wired connection or combinations thereof.

8. A diabetes manager of claim 1, further comprising a user input device selected from the group comprising: touchpad, touch pen, touch screen, keyboard, mouse, joystick, trackball, wireless mouse, pointing device and combinations thereof.

9. A diabetes manager of claim 1, wherein the graphical user interface is configured to display at least one input box for receipt of data relating to a carb ratio, insulin sensitivity and combinations thereof.

10. A diabetes manager for modifying insulin therapy support parameters including a start time of day data value, an end time of day data value, a lower blood glucose target data value, an upper blood glucose target data value, a high blood glucose warning data value and a low blood glucose warning data value on a hand-held diabetes management device comprising:

a graphical user interface module, a data store, and a data mapping module implemented on a non-transitory computer readable medium on a computing device, wherein the computing device communicates with a hand-held diabetes management device;

the graphical user interface module being configured to create a graphical user interface illustrating a bar chart having a plurality of bar structures, an x-axis graphically illustrating a time of day and a y-axis graphically illustrating a blood glucose level, the plurality of bar structures positionable on the bar chart, each of the plurality of bar structures having a first side that graphically indicates a start time of day opposite a second side that graphically indicates an end time of day and a third side that graphically indicates a lower target value for a blood glucose level opposite a fourth side that graphically indicates an upper target value for the blood glucose level;

the first side, the second side, the third side and the fourth side of each of the plurality of bar structures adjustable by a user input;

the third side of at least one of the plurality of bar structures spaced apart from the x-axis;

the data store being configured to store at least the a start time of day data value, an end time of day data value, a lower blood glucose target data value and an upper blood glucose target data value;

the data mapping module being configured to map for each of the plurality of bar structures on the graphical user interface the start time of day data value to a location of the first side, the end time of day data value to a location of the second side, the lower blood glucose target data value to a location of the third side and the upper blood glucose target data value to a location of the fourth side and stores the start time of day data value, the end time of day data value, the lower blood glucose target data value and the upper blood glucose target data value in the data store; and wherein the data mapping module is configured to output the start time of day data value, end time of day data value, lower blood glucose target data value and upper blood glucose target data value to the hand-held diabetes management device.

11. A diabetes manager of claim 10, wherein the graphical user interface is configured to create a first line that graphically illustrates an upper boundary limit and a second line that graphically illustrates a lower boundary limit, the first line and second line each being graphically illustrated on the bar chart as horizontal lines.

12. A diabetes manager of claim 11, wherein the first line and the second line are adjustable by a user input.

13. A diabetes manager of claim 12, wherein the data store is configured to store a high blood glucose warning data value and a low blood glucose warning data value, and the data mapping module is configured to map the high blood glucose warning data value to a location of the first line and the low blood glucose warning data value to a location of the second line.

14. A diabetes manager of claim 13, wherein the plurality of bar structures are governed by a set of constraints that confine each of the plurality of bar structures to an area defined by the first line and the second line.

15. A diabetes manager of claim 14, wherein the second line is positioned on the bar chart above the x-axis, such that the second line graphically represents a blood glucose level value greater than zero.

16. A diabetes manager of claim 14, wherein the first side and the second side of each of the plurality of bar structures cooperate to form a time window, and the set of constraints further confines the time window defined by the first side and the second side of each of the plurality of bar structures to a unique time window.

17. A diabetes manager of claim 10, wherein the hand-held diabetes management device is in communication with the computing device through a wireless connection, a wired connection or combinations thereof.

18. A diabetes manager of claim 10, wherein the graphical user interface is configured to display at least one input box for receipt of data relating to a carb ratio, insulin sensitivity and combinations thereof.

19. A diabetes manager of claim 10, wherein the number of the plurality of bar structures displayed on the graphical user interface is adjustable by user input.

* * * * *